US010556104B2

(12) United States Patent
Gerber

(10) Patent No.: US 10,556,104 B2
(45) Date of Patent: Feb. 11, 2020

(54) IMPLANTABLE MEDICAL ELONGATED MEMBER WITH ADHESIVE ELEMENTS

(71) Applicant: Medtronic, Inc., Minneapolis, MN (US)

(72) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 7 days.

(21) Appl. No.: 15/589,700

(22) Filed: May 8, 2017

(65) Prior Publication Data

US 2017/0281932 A1 Oct. 5, 2017

Related U.S. Application Data

(62) Division of application No. 11/591,443, filed on Oct. 31, 2006, now Pat. No. 9,643,004.

(51) Int. Cl.
*A61N 1/05* (2006.01)

(52) U.S. Cl.
CPC ............ *A61N 1/0558* (2013.01); *A61N 1/057* (2013.01)

(58) Field of Classification Search
CPC ........ A61N 1/05; A61N 1/057; A61N 1/0558; A61N 1/36007
See application file for complete search history.

(56) References Cited

U.S. PATENT DOCUMENTS 4,282,886 A 8/1981 King
4,360,031 A 11/1982 White
4,768,523 A 9/1988 Cahalan et al.
6,463,335 B1 10/2002 Munch et al.
6,510,347 B2 1/2003 Borkan
6,620,308 B2 9/2003 Gilbert
6,718,212 B2 4/2004 Parry et al.
6,889,091 B2 5/2005 Hine et al.
(Continued)

FOREIGN PATENT DOCUMENTS

EP 1180380 A2 2/2002
GB 2274995 A 8/1994
(Continued)

OTHER PUBLICATIONS

Examination Report from counterpart European Application No. 07749336.9-2305, dated Feb. 3, 2010, 3 pages.
(Continued)

*Primary Examiner* — Michael J D Abreu
(74) *Attorney, Agent, or Firm* — Shumaker & Sieffert, P.A.

(57) ABSTRACT

The disclosure is directed to securing electrodes of a medical lead adjacent to a target tissue site. The medical lead may include at least one adhesive element disposed along a longitudinal outer surface of the lead body to adhere the adjacent tissue to the lead. Adhesive elements may be disposed proximal to, distal to, or in-between the electrodes of the lead. Each adhesive element may be inactive during lead implantation and activated by removing a covering sheath to expose the adhesive elements to moisture in the tissue or presenting an energy, e.g. ultraviolet light, to the adhesive elements. Once active, the adhesive elements secure the lead to surrounding tissue to prevent migration of the electrodes from the target tissue.

19 Claims, 23 Drawing Sheets

10
16
26
CLINICIAN PROGRAMMER
13
14A
24
12
14
22
18
PATIENT PROGRAMMER
28
14B

(56) References Cited

U.S. PATENT DOCUMENTS

| | | | | |
|---|---|---|---|---|
| 6,978,180 | B2 | 12/2005 | Tadlock | |
| 7,099,718 | B1 | 8/2006 | Thacker et al. | |
| 7,130,700 | B2 | 10/2006 | Gardeski et al. | |
| 7,316,667 | B2 | 1/2008 | Lindstrom et al. | |
| 7,353,067 | B1 | 4/2008 | Helland et al. | |
| 8,688,238 | B2 | 4/2014 | Gerber | |
| 9,643,004 | B2 | 5/2017 | Gerber | |
| 2001/0023367 | A1 | 9/2001 | King et al. | |
| 2002/0198572 | A1* | 12/2002 | Weiner | A61N 1/0504 607/46 |
| 2003/0074041 | A1* | 4/2003 | Parry | A61N 1/0587 607/130 |
| 2003/0105506 | A1* | 6/2003 | Krishnan | A61N 1/056 607/126 |
| 2004/0097965 | A1 | 5/2004 | Gardeski et al. | |
| 2005/0096718 | A1* | 5/2005 | Gerber | A61N 1/0558 607/117 |
| 2005/0177220 | A1 | 8/2005 | Iaizzo et al. | |
| 2005/0222537 | A1 | 10/2005 | Dinsmoor et al. | |
| 2008/0103578 | A1 | 5/2008 | Gerber | |
| 2008/0103579 | A1* | 5/2008 | Gerber | A61N 1/0558 607/149 |

FOREIGN PATENT DOCUMENTS

| | | | |
|---|---|---|---|
| WO | 9943376 | A1 | 9/1999 |
| WO | 2005077266 | A1 | 8/2005 |

OTHER PUBLICATIONS

Examination Report from counterpart European Application No. 07749336.9-2305, dated Feb. 18, 2011, 5 pages.

Response to Extended Search Report dated Feb. 3, 2010, from counterpart European Application No. 07749336.9-2305, filed Jun. 2, 2010, 13 pp.

Response to Extended Search Report dated Feb. 18, 2011, from counterpart European Application No. 07749336.9-2305, filed Aug. 11, 2011, 9 pp.

Amended claims from counterpart European Application No. 07749336.9-2305 filed May 22, 2009, 9 pp.

International Search Report and Written Opinion of International Application No. PCT/US2007/002241, dated Aug. 7, 2007, 9 pp.

Response to Written Opinion dated Aug. 7, 2007, from International Application No. PCT/US2007/002241, dated Jun. 5, 2008, 17 pp.

International Preliminary Report on Patentability from International Application No. PCT/US2007/002241, dated Oct. 20, 2008, 10 pp.

Prosecution History from U.S. Appl. No. 11/591,443, dated Apr. 13, 2009 through Apr. 5, 2017, 162 pp.

Prosecution History from U.S. Appl. No. 11/591,433, dated Jul. 15, 2009 through Jun. 14, 2011, 54 pp.

Prosecution History from U.S. Appl. No. 11/591,450, dated Jun. 25, 2009 through Jan. 7, 2016, 134 pp.

* cited by examiner 52
58
54
56

52
58
59
54
56

IMPLANTABLE MEDICAL ELONGATED MEMBER WITH ADHESIVE ELEMENTS

This application is a divisional application of U.S. patent application Ser. No. 11/591,443, filed on Oct. 31, 2006 and entitled "IMPLANTABLE MEDICAL ELONGATED MEMBER WITH ADHESIVE ELEMENTS," the entire content of which is herein incorporated by reference.

TECHNICAL FIELD

The invention relates to stimulation systems, and more particularly, to stimulation leads in stimulation systems.

BACKGROUND

Neurostimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. An electrical stimulation system typically includes one or more stimulation leads coupled to a neurostimulator.

The stimulation lead may be percutaneously or surgically implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, stomach, bladder, or within a brain or other organ of a patient, or within a muscle or muscle group of a patient. The one or more electrodes located proximate to the target stimulation site may deliver electrical stimulation therapy to the target stimulation site in the form of electrical signals.

Electrical stimulation of a sacral nerve may eliminate or alleviate some pelvic floor disorders by influencing the behavior of the relevant structures, such as the bladder, sphincter and pelvic floor muscles. Pelvic floor disorders include urinary incontinence, urinary urge/frequency, urinary retention, pelvic pain, bowel dysfunction, and male and female sexual dysfunction. The organs involved in bladder, bowel, and sexual function receive much of their control via the second, third, and fourth sacral nerves, commonly referred to as S2, S3 and S4 respectively. Thus, in order to deliver electrical stimulation to at least one of the S2, S3, or S4 sacral nerves, a stimulation lead is implanted proximate to the sacral nerve(s).

Electrical stimulation of a peripheral nerve, such as stimulation of an occipital nerve, may be used to induce paresthesia. Occipital nerves, such as a lesser occipital nerve, greater occipital nerve or third occipital nerve, exit the spinal cord at the cervical region, extend upward and toward the sides of the head, and pass through muscle and fascia to the scalp. Pain caused by an occipital nerve, e.g. occipital neuralgia, may be treated by implanting a lead proximate to the occipital nerve to deliver stimulation therapy.

In many stimulation applications, it is desirable for a stimulation lead to resist migration following implantation. For example, it may be desirable for the electrodes disposed at a distal end of the implantable medical lead to remain proximate to a target stimulation site in order to provide adequate and reliable stimulation of the target stimulation site. In some applications, it may also be desirable for the electrodes to remain substantially fixed in order to maintain a minimum distance between the electrode and a nerve in order to help prevent inflammation to the nerve and in some cases, unintended nerve damage. Securing the stimulation lead at the target stimulation site may minimize lead migration.

SUMMARY

In general, the invention is directed toward securing an elongated member adjacent to a target tissue site. The elongated member is configured to be coupled to a medical device to deliver a therapy from the medical device to target therapy delivery site in a patient. The therapy may be electrical stimulation, drug delivery, or both. The elongated member includes at least one adhesive element disposed along a longitudinal outer surface of the elongated member. The at least one adhesive element adheres to adjacent tissue to substantially fix a position of the elongated member.

Each adhesive element may be inactive during lead implantation to prevent premature fixation of the elongated member. The adhesive elements may be activated by removing a covering sheath to expose the adhesive elements to moisture in the tissue. Alternatively, the adhesive elements may be activated by presenting an energy, e.g. ultraviolet light, to the adhesive elements via one or more conduits within the lead body. Once active, the adhesive elements secure the lead to prevent migration of the electrodes from the target tissue.

In one embodiment, the disclosure is directed to a medical lead that includes an elongated member having a proximal end and a distal end and defining a longitudinal outer surface, at least one electrode disposed closer to the distal end of the elongated member than the proximal end, and an adhesive element disposed on the longitudinal outer surface of the elongated member.

In another embodiment, the disclosure is directed to a method that includes inserting a medical elongated member into a patient, wherein the elongated member comprises at least one electrode and an adhesive element disposed on a longitudinal outer surface of the elongated member, positioning the elongated member adjacent to a target therapy delivery site, and activating the adhesive element to secure the elongated member adjacent to the target therapy delivery site.

In an additional embodiment, the disclosure is directed to a system that includes a medical lead having an elongated member having a proximal end, a distal end, and defining a longitudinal outer surface, at least one electrode disposed closer to the distal end than the proximal end, and an adhesive element disposed on the longitudinal outer surface of the elongated member. The system also includes an electrical stimulator that delivers electrical stimulation therapy to a patient via the medical lead implanted within the patient.

In another additional embodiment, the disclosure is directed to an apparatus that includes an implantable medical elongated member configured to couple to a medical device to deliver a therapy from the medical device to a target therapy delivery site in a patient and defining a longitudinal outer surface and an adhesive element disposed on the longitudinal outer surface of the elongated member to secure the apparatus to a tissue of the patient.

The disclosure may provide one or more advantages. For example, the adhesive elements disposed along the outer surface of the lead body may be simple to employ and implant. The clinician may, with one motion, activate the adhesive elements by removing a covering sheath. Alternatively, the adhesive elements may be activated and/or cured with ultraviolet light that is transmitted down the lead to the elements from a proximal light source. In any case, the adhesive elements may be strategically placed on the lead for a customizable adhesion pattern to fix certain tissues or avoid other tissues.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
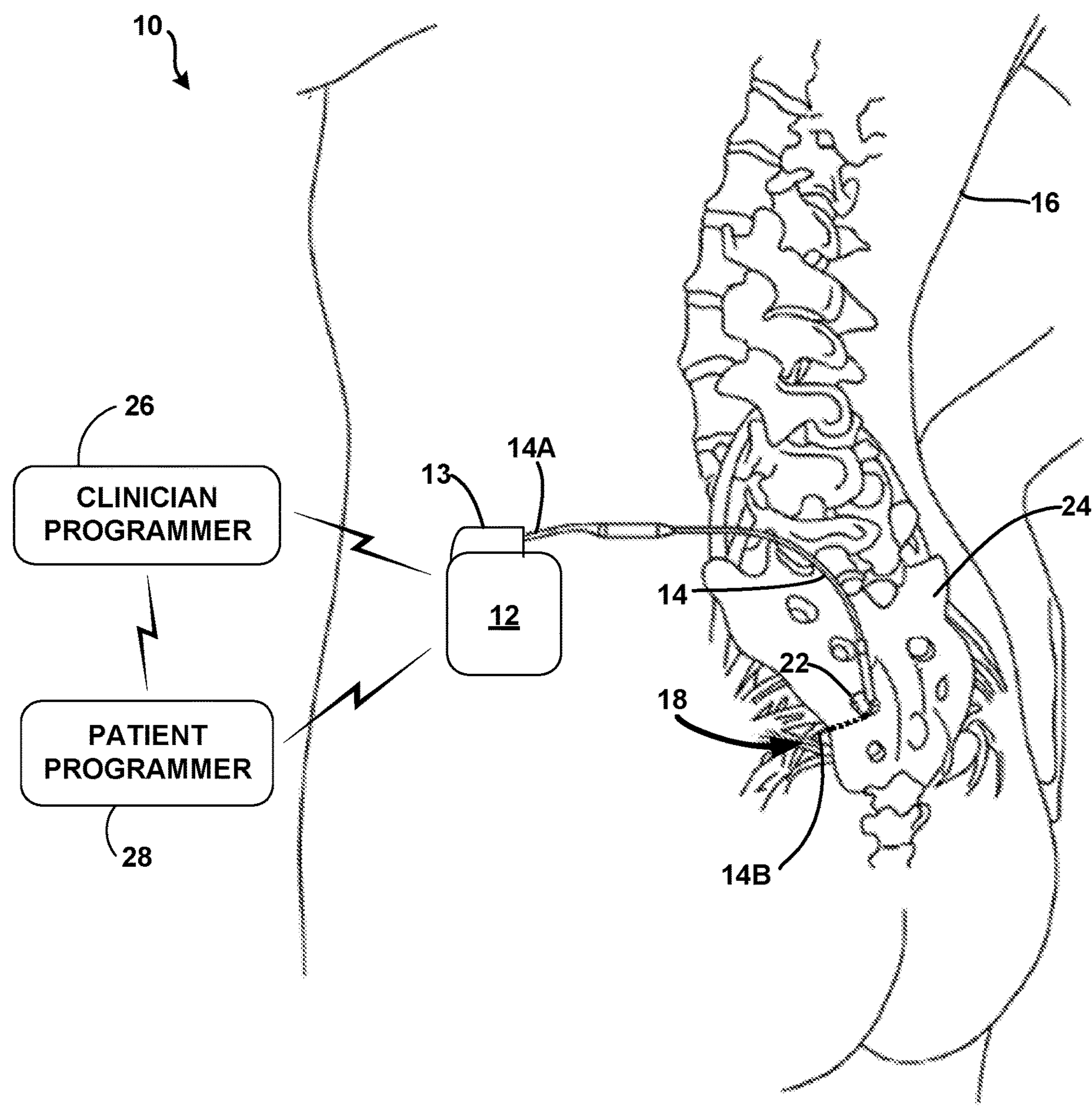
FIG. 1A is a schematic perspective view of a therapy system, which includes an electrical stimulator coupled to a stimulation lead, which has been implanted in a body of a patient proximate to a target stimulation site.

The disclosure is directed to an implantable medical elongated member that is configured to secure the elongated member at a specific tissue location within a patient. The specific tissue location may be, for example, a target stimulation site or a target drug delivery site. The elongated member is configured to be coupled to a medical device to deliver a therapy from the medical device to target tissue in a patient. Various embodiments of the elongated member may be applicable to different therapeutic applications. For example, the elongated member may be an electrical stimulation lead that is used to deliver electrical stimulation to a target stimulation site and/or sense parameters (e.g., blood pressure, temperature or electrical activity) of a patient. In another embodiment, the elongated member may be a catheter that is placed to deliver a fluid, such as pharmaceutical agents, insulin, pain relieving agents, gene therapy agents or the like from a fluid delivery device (e.g., a fluid reservoir and/or pump) to a target tissue site in a patient. The invention is applicable to any configuration or type of implantable elongated member that is used to deliver therapy to a site in a patient. For purposes of illustration, however, the disclosure will refer to a stimulation lead. Thus, while the embodiments described herein are directed to stimulation leads, a drug delivery catheter or any other therapy lead may utilize the securing methods to reduce migration of the lead from a target tissue site.

Leads are generally implanted within a patient such that electrodes at the distal portion of the lead may reside adjacent to one or more nerves or tissue region to be stimulated (i.e., the target tissue site or target therapy delivery site). As the patient moves with normal activity, the lead may migrate within the patient unless the lead is secured to the targeted tissue site. Therefore, lead embodiments described herein include a solidifying substance, such as a hardenable material to form fixation structures or an adhesive, which provides one or more fixation elements to anchor at least a portion of the longitudinal outer surface of the lead to the tissue site. The longitudinal outer surface is the surface of the lead that is generally parallel to the central axis of the lead. For example, the longitudinal outer surface of a cylindrical lead is the circumferential surface that is curved to create the cylindrical lead. The fixation element of the lead is constructed to help prevent premature fixation of the lead (i.e., before the lead is positioned correctly within a patient).

In one embodiment, the solidifying substance is delivered through a conduit disposed within a lead body of the lead and exits out of an exit port defined by a longitudinal outer surface of the lead body. The solidifying substance may be activated by heat or moisture, from patient 16 or external sources. For example, the solidifying substance may be an adhesive that is cured or a solidifying substance that is hardened to create a fixation element that extends away from the lead. In some embodiments, the exit port is covered by a balloon element that is inflated by the solidifying substance, which is delivered to the balloon element via the exit port. In the inflated state, the balloon element defines a fixation element that extends from the lead body to engage with surrounding tissue. In some cases, the solidifying substance may include a first fluid and a second fluid that solidify or otherwise cure upon combining together.

In another embodiment, the lead includes one or more adhesive elements, e.g., a fixation element, disposed on the longitudinal outer surface of the lead. The adhesive elements may be activated by moisture. For example, upon implantation of the lead in a patient, a clinician may withdraw a sheath to expose the adhesive elements, thereby exposing the adhesive elements to moisture from surrounding tissue. The moisture may interact with the adhesive element to activate the adhesive properties of the adhesive elements. Alternatively, the adhesive elements may be activated by an energy source, such as thermal energy or ultraviolet (UV) light, delivered to the adhesive elements though a conduit within the lead. Once the adhesive elements are activated, the adhesive elements bond to the adjacent tissue and secure the lead within the patient. In addition, an energy may be used to deactivate the adhesive elements when the lead is to be removed from patient 16.

FIG. 1A a schematic perspective view of a therapy system 10, which includes neurostimulator 12 coupled to stimulation lead 14. Neurostimulator 12 may be implantable or external. For example, neurostimulator 12 may be subcutaneously implanted in the body of a patient (e.g., in a chest cavity, lower back, lower abdomen, or buttocks of patient 20 (not shown in FIG. 1A)). Neurostimulator 12 provides a programmable stimulation signal (e.g., in the form of electrical pulses or substantially-continuous-time signals) that is delivered to target stimulation site 18 by stimulation lead 14, and more particularly, via one or more stimulation electrodes carried by lead 14. In some embodiments, neurostimulator 12 may be coupled to two or more leads, e.g., for bilateral or multi-lateral stimulation. Neurostimulator 12 may also be referred to as a pulse generator. In some embodiments, lead 14 may also carry one or more sense electrodes to permit neurostimulator 12 to sense electrical signals from target stimulation site 18.

Lead 14 further includes a lead body and one or more fixation elements (not shown in FIG. 1) which engage with tissue proximate to target stimulation site 18 to substantially fixed a position of lead 14 proximate to target stimulation site 18. The one or more fixation elements are formed in situ (i.e., after lead 14 is implanted in patient 16) and may be, for example, an adhesive element, a fixation structure or a solidifying substance. Proximal end 14A of lead 14 may be both electrically and mechanically coupled to connector 13 of neurostimulator 12 either directly or via a lead extension. In particular, conductors disposed in the lead body electrically connect stimulation electrodes (and sense electrodes, if present) at adjacent to distal end 14B of lead 14 to neurostimulator 12.

In the embodiment of therapy system 10 shown in FIG. 1A, target stimulation site 18 is proximate to the S3 sacral nerve, and lead 14 has been introduced into the S3 sacral foramen 22 of sacrum 24 to access the S3 sacral nerve. Stimulation of the S3 sacral nerve may help treat pelvic floor disorders, urinary control disorders, fecal control disorders, interstitial cystitis, sexual dysfunction, and pelvic pain. Therapy system 10, however, is useful in other stimulation applications. In particular, stimulation lead 14 in accordance with the invention may be adapted for application to a variety of electrical stimulation applications. Thus, in alternate embodiments, target stimulation site 18 may be a location proximate to any of the other sacral nerves in body 16 or any other suitable nerve in body 16, which may be selected based on, for example, a therapy program selected for a particular patient. For example, in other embodiments, therapy system 10 may be used to deliver stimulation therapy to pudendal nerves, perineal nerves, or other areas of the nervous system, in which cases, lead 14 would be implanted and substantially fixed proximate to the respective nerve. As further alternatives, lead 14 may be positioned for temporary or chronic spinal cord stimulation for the treatment of pain, peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), mitigation of other peripheral and localized pain (e.g., leg pain or back pain), or for deep brain stimulation to treat movement disorders and other neurological disorders.

Migration of lead 14 following implantation may be undesirable, and may have detrimental effects on the quality of therapy delivered to a patient 16. For example, migration of lead 10 may cause displacement of electrodes carried by lead 14 to a target stimulation site 18. In such a situation, the electrodes may not be properly positioned to deliver therapy to target stimulation site 18, resulting in reduced electrical coupling, and possibly undermining therapeutic efficacy of the stimulation therapy from system 10. Substantially fixing lead 14 to surrounding tissue may help discourage lead 14 from migrating from target stimulation site 18 following implantation, which may ultimately help avoid harmful effects that may result from a migrating stimulation lead 14.

To that end, the invention provides lead 14 with either a solidifying substance or adhesive (not shown in FIG. 1) to provide fixation between lead 14 and tissue surrounding lead 14, such as tissue proximate to target stimulation site 18 in the example of FIG. 1A. In comparison to some existing methods of fixing implanted medical leads, such as suturing lead 14 to surrounding tissue, the in situ securing methods of a solidifying substance or adhesive may permit implantation of lead 14 in patient 16 via a minimally invasive surgery, which may allow for reduced pain and discomfort for patient 16 relative to surgery, as well as a quicker recovery time. As described in further detail below, the in situ fixation elements are configured to secure at least a portion of the longitudinal outer surface of lead 14 to adjacent tissue upon either activation of the solidifying substance or adhesive or upon delivery of the solidifying substance or adhesive to the longitudinal outer surface of lead 14. The in situ fixation may reduce implantation time and tissue damage from the fixation.

In accordance with the invention, in situ fixation of lead 14 may be achieved via any suitable technique. For example, in one embodiment, a solidifying substance is delivered to the longitudinal surface of lead 14 via a conduit and exit port defined by the longitudinal surface of lead 14. The solidifying substance may be an adhesive that spreads out and bonds lead 14 to the surrounding tissue when moisture from the tissue cures, or activates, the solidifying substance. The solidifying substance may also quickly cure as it leaves the exit port to form a fixation structure that extends from the longitudinal surface of lead 14. In addition, the solidifying substance may fill and inflate a balloon element to allow the balloon element to extend from lead 14 and engage with surrounding tissue to secure lead 14 in place. In another embodiment, in situ fixation of lead 14 is achieved with an adhesive that is disposed at one or more locations around the longitudinal outer surface of lead 14. The adhesive may be activated when exposed to moisture by removing a sheath or when exposed to energy delivered within 14 lead.

Therapy system 10 also may include a clinician programmer 26 and a patient programmer 28. Clinician programmer 26 may be a handheld computing device that permits a clinician to program stimulation therapy for patient 16, e.g., using input keys and a display. For example, using clinician programmer 26, the clinician may specify stimulation parameters for use in delivery of stimulation therapy. Clinician programmer 26 supports telemetry (e.g., radio frequency telemetry) with neurostimulator 12 to download stimulation parameters and, optionally, upload operational or physiological data stored by neurostimulator 12. In this manner, the clinician may periodically interrogate neurostimulator 12 to evaluate efficacy and, if necessary, modify the stimulation parameters.

Like clinician programmer 26, patient programmer 28 may be a handheld computing device. Patient programmer 28 may also include a display and input keys to allow patient 16 to interact with patient programmer 28 and implantable neurostimulator 12. In this manner, patient programmer 28 provides patient 16 with an interface for control of stimulation therapy by neurostimulator 12. For example, patient 16 may use patient programmer 28 to start, stop or adjust stimulation therapy. In particular, patient programmer 28 may permit patient 16 to adjust stimulation parameters such as duration, amplitude, pulse width and pulse rate, within an adjustment range specified by the clinician via clinician programmer 28, or select from a library of stored stimulation therapy programs.

Neurostimulator 12, clinician programmer 26, and patient programmer 28 may communicate via cables or a wireless communication, as shown in FIG. 1A. Clinician programmer 26 and patient programmer 28 may, for example, communicate via wireless communication with neurostimulator 12 using RF telemetry techniques known in the art. Clinician programmer 26 and patient programmer 28 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Figure 1B:
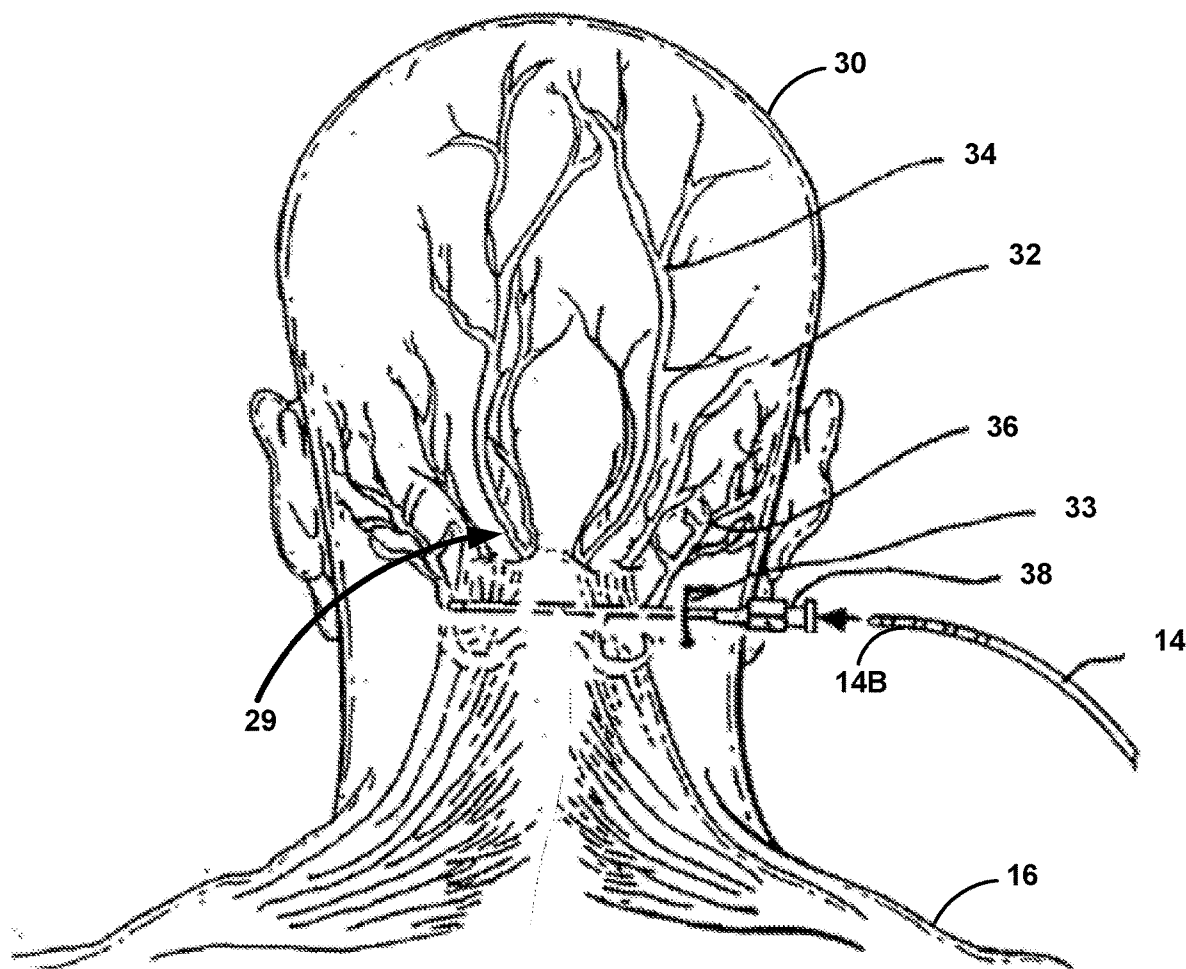
FIG. 1B is an illustration of the implantation of a stimulation lead at a location proximate to an occipital nerve.

FIG. 1B is a conceptual illustration of an alternative implantation site for lead 14 of FIG. 1A. Therapy system 10 may also be used to provide stimulation therapy to other nerves of a patient 16. For example, as shown in FIG. 1B, lead 14 may be implanted and fixated with one or more in situ fixation elements proximate to an occipital region 29 of patient 30 for stimulation of one or more occipital nerves. In particular, lead 14 may be implanted proximate to lesser occipital nerve 32, greater occipital nerve 34, and third occipital nerve 36. In FIG. 1B, lead 14 is aligned to be introduced into an introducer needle 38 in order to be implanted and anchored or fixated with the an adhesive or one or more in situ formed fixation structures proximate to occipital region 29 of patient 30. A neurostimulator (e.g., neurostimulator 12 in FIG. 1A) may deliver stimulation therapy to any one or more of occipital nerve 32, greater occipital nerve 34 or third occipital nerve 36 via electrodes disposed adjacent to distal end 14B of lead 14. In alternate embodiments, lead 14 may be positioned proximate to one or more other peripheral nerves proximate to occipital nerves 32, 34, and 36 of patient 30, such as nerves branching from occipital nerves 32, 34, and 36, as well as stimulation of any other suitable nerves throughout patient 30, such as, but not limited to, nerves within a brain, stomach or spinal cord of patient 30.

Implantation of lead 14 may involve the subcutaneous placement of lead 14 transversely across one or more occipital nerves 32, 34, and/or 36 that are causing patient 30 to experience pain. In one example method of implanting lead 14 proximate to the occipital nerve, using local anesthesia, a vertical skin incision 33 approximately two centimeters in length is made in the neck of patient 30 lateral to the midline of the spine at the level of the C1 vertebra. The length of vertical skin incision 33 may vary depending on the particular patient. At this location, the patient's skin and muscle are separated by a band of connective tissue referred to as fascia. Introducer needle 38 is introduced into the subcutaneous tissue, superficial to the fascia and muscle layer but below the skin. Occipital nerves 32, 34, and 36 are located within the cervical musculature and overlying fascia, and as a result, introducer needle 38 and, eventually, lead 14 are inserted superior to occipital nerves 32, 34, and 36.

Once introducer needle 38 is fully inserted, lead 14 may be advanced through introducer needle 38 and positioned to allow stimulation of the lesser occipital nerve 32, greater occipital nerve 34, third occipital nerve 36, and/or other peripheral nerves proximate to an occipital nerve. Upon placement of lead 14, introducer needle 38 may be removed. In some embodiments, introducer needle 38 may be used to remove lead 14 after stimulation therapy is no longer needed.

Accurate lead placement may affect the success of occipital nerve stimulation. If lead 14 is located too deep, i.e., anterior, in the subcutaneous tissue, patient 30 may experience muscle contractions, grabbing sensations, or burning. Such problems may additionally occur if lead 14 migrates after implantation. Furthermore, due to the location of implanted lead 14 on the back of the neck of patient 30, lead 14 may be subjected to pulling and stretching that may increase the chances of lead migration. The in situ formed fixation elements of lead 14 help minimize the migration of lead 14 following implantation proximate to occipital nerve site 29, thereby minimizing the aforementioned adverse effects attributable to lead migration.

A "target tissue site" is referenced throughout the remainder of the disclosure. The target tissue site may be target stimulation site 18 shown in FIG. 1A, occipital nerve site 29 shown in FIG. 1B or any other suitable stimulation site or therapy delivery site in a patient, including a variety of organs and muscles within the body of a patient.

Figure 2:
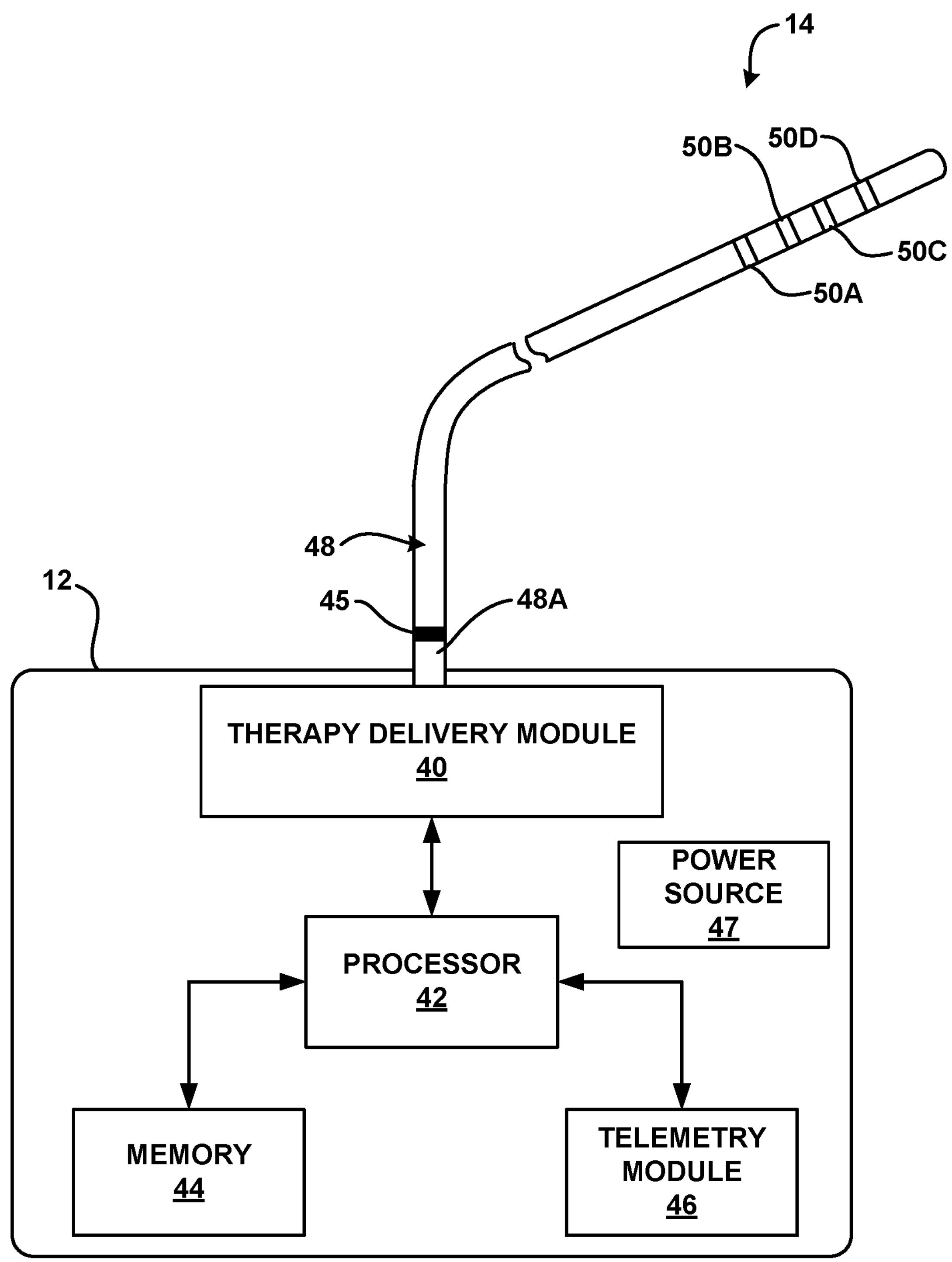
FIG. 2 is a block diagram illustrating various components of an electrical stimulator and an implantable lead.

FIG. 2 is a block diagram illustrating various components of implantable neurostimulator 12 and an implantable lead 14. Neurostimulator 12 includes therapy delivery module 40, processor 42, memory 44, telemetry module 46, and power source 47. In some embodiments, neurostimulator 12 may also include a sensing circuit (not shown in FIG. 2). Implantable lead 14 includes lead body 48 extending between proximal end 48A and distal end 48B. Lead body 48 may be a cylindrical or may be a paddle-shaped (i.e., a "paddle" lead). When lead body 48 is cylindrical, lead body 48 defines a longitudinal outer surface that is generally the surface extending between proximal end 48A and distal end 48B of lead body 48. If lead body 48 is non-cylindrical, the longitudinal outer surface is generally the longest dimension of the lead body. Electrodes 50A, 50B, 50C, and 50D (collectively "electrodes 50") are disposed on lead body 48 adjacent to distal end 48B of lead body 48.

In some embodiments, electrodes 50 may be ring electrodes. In other embodiments, electrodes 50 may be segmented or partial ring electrodes, each of which extends along an arc less than 360 degrees (e.g., 90-120 degrees) around the circumference of lead body 48. In embodiments in which lead 14 is a paddle lead, electrodes 50 may extend along a portion of the periphery defined by lead body 48. Electrodes 50 are electrically coupled to a therapy delivery module 40 of neurostimulator 12 via conductors within lead body 48. The configuration, type, and number of electrodes 50 illustrated in FIG. 2 are merely exemplary.

Electrodes 50 extending around a portion of the circumference of lead body 48 or along one side of a paddle lead may be useful for providing electrical stimulation in a particular direction/targeting a particular therapy deliver site. For example, in the electrical stimulation application shown in FIG. 1B, electrodes 50 may be disposed along lead body 48 such that the electrodes face toward occipital nerves 32, 34, and/or 36, or otherwise away from the scalp of patient 30. This may be an efficient use of stimulation because electrical stimulation of the scalp may not provide any efficacious therapy to patient 30.

In embodiments in which electrodes 50 extend around a portion of the circumference of lead body 48 or along one side of a paddle lead, lead 14 may include one or more orientation markers 45 proximate to proximal end 14A that indicate the relative location of electrodes 50. Orientation marker 45 may be a printed marking on lead body 48, an indentation in lead body 48, a radiographic marker, or another type of marker that is visible or otherwise detectable (e.g., detectable by a radiographic device) by a clinician. Orientation marker 45 may help a clinician properly orient lead 14 such that electrodes 50 face the desired direction (e.g., toward occipital nerves 32, 34, and/or 36) within patient 16. For example, orientation marker 45 may also extend around the same portion of the circumference of lead body 48 or along the side of the paddle lead as electrodes 50. In this way, orientation marker 45 faces the same direction as electrodes, thus indicating the orientation of electrodes 50 to the clinician. When the clinician implants lead 14 in patient 16, orientation marker 45 may remain visible to the clinician.

Neurostimulator 12 delivers stimulation therapy via electrodes 50 of lead 14. In one embodiment, an implantable signal generator or other stimulation circuitry within therapy delivery module 40 delivers electrical signals (e.g., pulses or substantially continuous-time signals, such as sinusoidal signals) to targets tissue site via at least some of electrodes 50 under the control of a processor 42. The stimulation energy generated by therapy delivery module 40 may be formulated as stimulation energy, e.g., for treatment of any of a variety of neurological disorders, or disorders influenced by patient neurological response. The signals may be delivered from therapy delivery module 40 to electrodes 50 via a switch matrix and conductors carried by lead 14 and coupled to respective electrodes 50.

Neurostimulator 12 delivers stimulation therapy via electrodes 50 of lead 14. In one embodiment, an implantable signal generator or other stimulation circuitry within therapy delivery module 40 delivers electrical signals to a target tissue site via at least some of electrodes 50 under the control of a processor 42. The stimulation energy generated by therapy delivery module 40 may be formulated as stimulation energy, e.g., for treatment of any of a variety of neurological disorders, or disorders influenced by patient neurological response. The signals may be delivered from therapy delivery module 40 to electrodes 50 via a switch matrix and conductors carried by lead 14 and electrically coupled to respective electrodes 50. The implantable signal generator may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power.

Processor 42 may include a microprocessor, a controller, a DSP, an ASIC, an FPGA, discrete logic circuitry, or the like. Processor 42 controls the implantable signal generator within therapy delivery module 40 to deliver stimulation therapy according to selected stimulation parameters. Specifically, processor 42 controls therapy delivery module 40 to deliver electrical signals with selected amplitudes, pulse widths (if applicable), and rates specified by the programs. In addition, processor 42 may also control therapy delivery module 40 to deliver the stimulation signals via selected subsets of electrodes 50 with selected polarities. For example, electrodes 50 may be combined in various bipolar or multi-polar combinations to deliver stimulation energy to selected sites, such as nerve sites adjacent the spinal column, pelvic floor nerve sites, or cranial nerve sites.

In addition, processor 42 may control therapy delivery module 40 to deliver each signal according to a different program, thereby interleaving programs to simultaneously treat different symptoms or provide a combined therapeutic effect. For example, in addition to treatment of one symptom such as sexual dysfunction, neurostimulator 12 may be configured to deliver stimulation therapy to treat other symptoms such as pain or incontinence.

Memory 44 of neurostimulator 12 may include any volatile or non-volatile media, such as a RAM, ROM, NVRAM, EEPROM, flash memory, and the like. In some embodiments, memory 44 of neurostimulator 12 may store multiple sets of stimulation parameters that are available to be selected by patient 16 or a clinician for delivery of stimulation therapy. For example, memory 44 may store stimulation parameters transmitted by clinician programmer 26 (FIG. 1A). Memory 44 also stores program instructions that, when executed by processor 42, cause neurostimulator 12 to deliver stimulation therapy. Accordingly, computer-readable media storing instructions may be provided to cause processor 42 to provide functionality as described herein.

In particular, processor 42 controls telemetry module 170 to exchange information with an external programmer, such as clinician programmer 26 and/or patient programmer 28 (FIG. 1A), by wireless telemetry. In addition, in some embodiments, telemetry module 46 supports wireless communication with one or more wireless sensors that sense physiological signals and transmit the signals to neurostimulator 12.

Figure 3A:
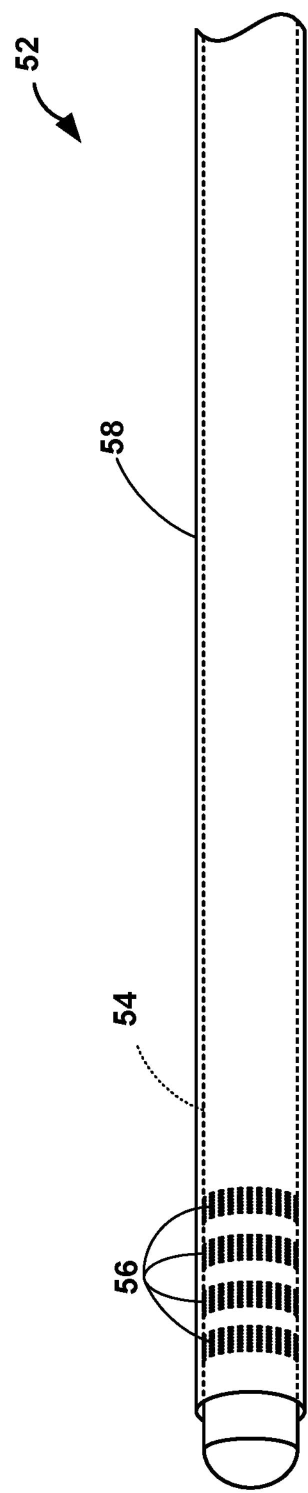
FIGS. 3A and 3B are perspective drawings of a sheath that covers a lead prior to implantation and removed after the lead is correctly positioned in a patient.
Figure 3B:
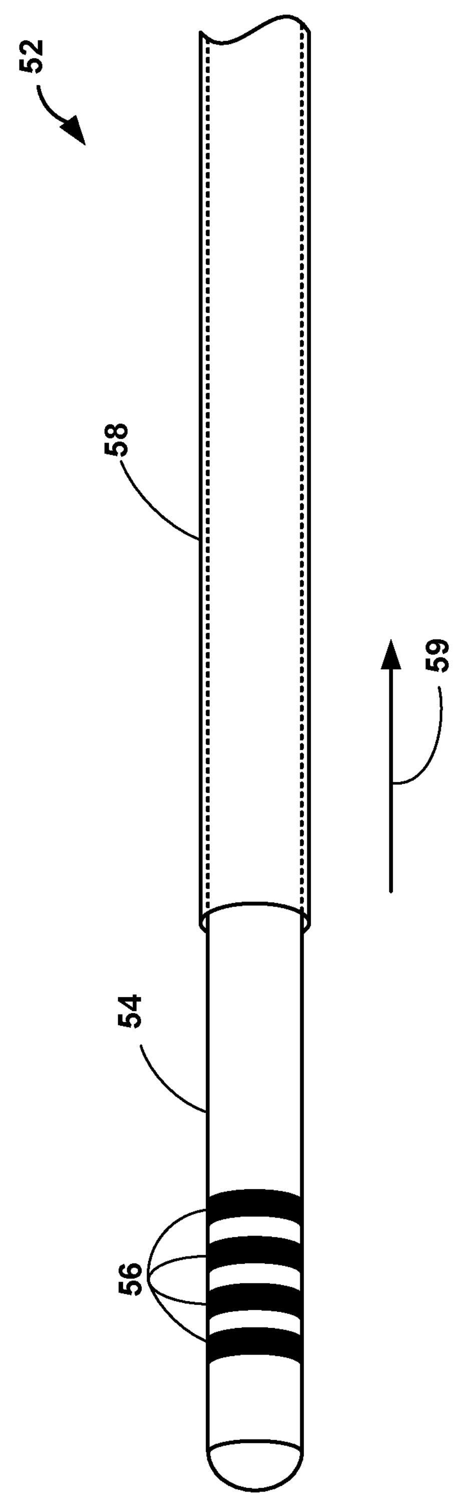

FIGS. 3A and 3B are perspective drawings of a sheath that covers a lead prior to implantation and is removed after the lead is correctly positioned in a patient. In particular, FIGS. 3A and 3B illustrate lead 52, which may be an embodiment of any lead described herein, including lead 14. Lead 52 includes lead body 54 (shown in phantom lines) extending between a proximal end (not shown in FIG. 3A) and distal end 54A, and electrodes 56 coupled to lead body 54 proximate to distal end 54A. The proximal end of lead body 48 typically includes electrical contacts (not shown in FIGS. 3A and 3B) to electrically couple lead 14 (and in particular, electrodes 56) to a lead extension or a neurostimulator (e.g., neurostimulator 12 in FIG. 1). As shown in FIG. 3A, lead 52 is capable of delivering electrical stimulation to numerous tissue sites within patient 16 via electrodes 56. Electrodes 56 are typically ring electrodes, but other types of electrodes may be used. For example, segmented electrodes, or multiple electrodes around the circumference of lead body 54 may be employed. Alternatively, lead 52 may be in a non-circular shape, such as a rectangular paddle lead.

Prior to delivering stimulation, at least a portion of lead body 54 of lead 52 is covered with sheath 58. In the embodiment shown in FIG. 3A, sheath 58 is constructed to protect electrodes 56 and any fixation elements from implantation stresses and/or to prevent the fixation elements from damaging adjacent tissues as lead 52 is implanted in patient 16. In addition, sheath 58 may be a restriction mechanism that keeps the fixation elements from being deployed or otherwise activated until a clinician removes the sheath.

Sheath 58 may be constructed of a flexible polymer or any other suitable material that provides a smooth interface between sheath 58 and lead body 54. In other embodiments, sheath 58 may be constructed of Teflon or other non-stick material that covers already activated adhesive elements and can be removed without affecting the placement of the adhesive elements. Further, sheath 58 outer surface may be coated with a lubricant to aid insertion. Sheath 58 may be sized to receive lead body 54, or alternatively, sheath 58 may be shrunk fit around lead body 54 to provide a snug fit between sheath 58 and the longitudinal outer surface of lead body 54 during an implantation procedure. In some embodiments, sheath 58 may be constructed to assist the clinician in guiding lead 52 within patient 16. In this case, sheath 58 may be similar to a lead introducer or cannula introduction device.

FIG. 3B shows lead 52 with sheath 58 being removed from lead body 54 in a direction indicated by arrow 59. Once lead 52 is positioned such that electrodes 56 are adjacent to a target tissue site, the clinician may begin removing lead 52 as shown. As sheath 58 is removed, one or more fixation elements may be exposed to the adjacent tissue to fix lead body 54 in position. The fixation elements may include balloon elements, fixation structures, adhesives, or other in situ formed or activated fixation elements discussed herein. In other embodiments, the clinician may remove sheath 58 in sections as fixation elements need to be deployed or as necessary to ensure proper fixation within the patient.

As previously discussed, a lead in accordance with the invention may be fixed at a target stimulation site with one or more fixation elements that are formed after the lead is implanted in a patient (i.e., in situ). In one embodiment, the one or more fixation elements are formed by delivering a solidifying material to a longitudinal outer surface of a lead body of the lead via one or more conduits that are in fluidic communication with one or more exit ports defined by the longitudinal outer surface.

Figure 4A:
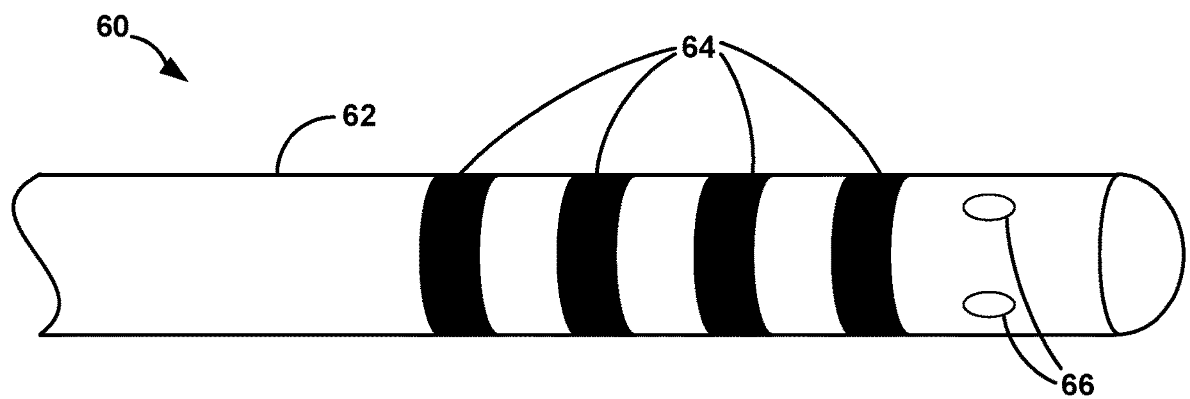
FIGS. 4A-4C are perspective drawings illustrating exemplary stimulation leads with varying configurations of exit ports that present a solidifying substance to secure the lead.
Figure 4B:
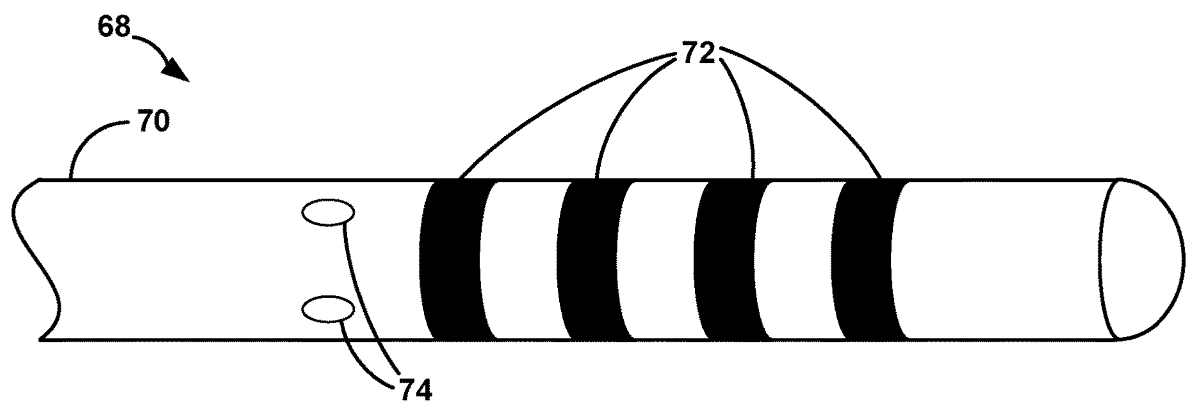
Figure 4C:
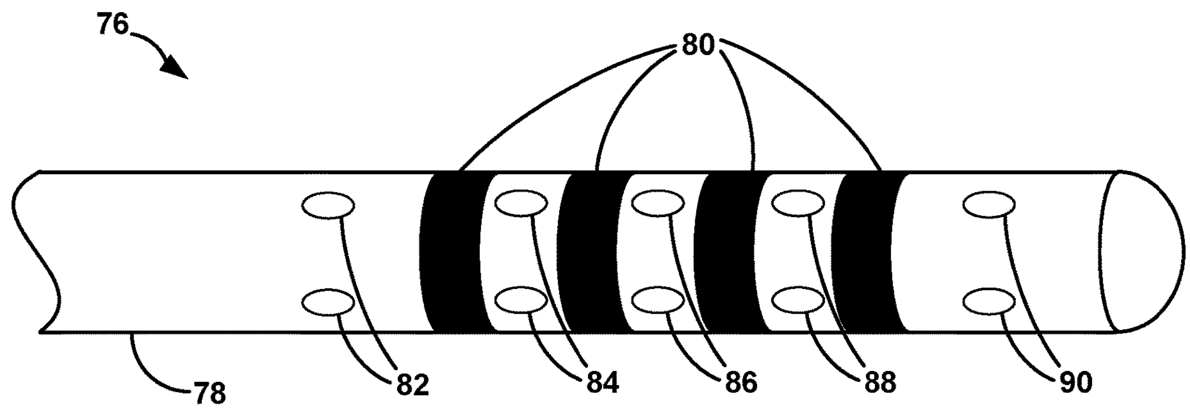

FIGS. 4A-4C are perspective drawings illustrating exemplary stimulation leads with varying configurations of exit ports that present a solidifying substance to secure the respective lead to surrounding tissue. As shown in FIG. 4A, lead 60 includes lead body 62, electrodes 64, and exit ports 66. Lead 60 is an embodiment of lead 14. Lead 60 may also include additional exit ports opposing exit ports 66 that cannot be seen from the perspective of FIG. 4A. Lead body 62 is generally cylindrical in shape with a distal and proximal end. The proximal end (not shown) of lead body 62 is configured to be connected to a neurostimulator that generates electrical stimulation delivered by lead 60. The distal end of lead body 62 is shown in FIG. 4A, as the four electrodes 64 are disposed near the distal end of lead body 62. Electrodes 64 are ring electrodes that extend around the entire circumference of lead body 62. Each electrode 64 may be programmed to be an anode or cathode controlled with particular stimulation parameters that may include pulse width, frequency, current amplitude, and voltage amplitude. In some embodiments, electrodes 64 may be constructed into a different shape, such as only partially wrapped around the circumference of lead body 62 or to accommodate the surface structure of the particular lead (e.g., in the case of a paddle lead, electrodes 64 may each be disposed on one side of the paddle lead.

For electrical stimulation provided by electrodes 64 to be effective, electrodes 64 must be placed adjacent to the target tissue site or otherwise in operative relation to a target tissue site. Without any fixation devices, lead 60 may move, or migrate, within patient 16 as the patient moves or neurostimulator 12 moves with respect to the distal end of lead 60. If electrodes 64 migrate to a location adjacent to non-target tissue, the electrical stimulation therapy may be ineffective and side effects may occur from the errant stimulation. For this reason, lead 60 includes exit ports 66 distal to electrodes 64 that provide an opening for the delivery of a solidifying substance to the tissue adjacent to the distal end of lead 60 to fix lead 60 at the target tissue site. In the example of FIG. 4A, the solidifying substance may be an adhesive that cures between lead body 62 and the surrounding tissue to secure lead 60 and prevent electrodes 64 from migrating away from the target tissue site. In some embodiments, the solidifying substance may not need to become completely solid for lead 60 to be secured to the adjacent tissue. For example, the solidifying substance may be an adhesive that remains partially tacky, or a semi-solid.

The solidifying substance travels through one or more conduits (shown in FIGS. 6A and 7A) within lead body 62 until the substance exits lead body 62 through exit ports 66. When the substance is an adhesive, curing, e.g., some degree of hardening, of the adhesive may be activated when the adhesive comes into contact with moisture from the surrounding tissue. Therefore, the solidifying substance may flow freely within lead body 62 and spread out between lead body 62 and adjacent tissue to adhere lead 62 body to the tissue. Once the water from the surrounding tissue encounters the solidifying substance, the substance turns into an adhesive that secures lead 60 to the tissue. Exemplary solidifying substances may include 2-octyl cyanoacrylate which is cured upon contact with water or fibrin glue which solidifies when the two components are combined.

In some embodiments, the solidifying substance may include more than one component. For example, two fluids may be used that, when combined, cure to form an adhesive to secure lead 60 to adjacent tissue. This two fluid system may be similar to a two-component epoxy adhesive system in which curing only occurs when the two-components are combined. The two fluids may be delivered by separate conduits that merge at each exit port 66. Alternatively, one exit port 66 may deliver one of the two fluids while the other exit port 66 delivers the second of the two fluids. The two fluids, e.g., fibrinogen and thrombin in the case of fibrin glue, may meet at the lead body 62 and tissue interface between the two exit ports 66 to form the solidifying substance and adhere the tissue to the lead body surface. In any case, the solidifying substance flows out of exit ports 66 to secure the distal region of lead body 62 to the surrounding tissue. In other embodiments, the solidifying substance may include more than two fluids that are combined to form a curing adhesive.

FIG. 4B shows lead 68, which includes lead body 70, electrodes 72 disposed near the distal end of lead body 70, and exit ports 74. Exit ports 74 are substantially similar to exit ports 66 of FIG. 4A, except that exit ports 74 are located proximal to electrodes 72. Proximally located exit ports 74 may allow electrodes 72 to be secured to the tissue by the solidifying substance without affecting tissue at the distal end of lead 68. There may be four exit ports 74 (two exit ports not viewable in the perspective of FIG. 4B), but other embodiments may include any number of exit ports around the circumference of lead body 70. In addition, exit ports 74 may be disposed at any axial location away from the distal electrode of electrodes 72. However, it may be beneficial to separate exit ports 74 from electrodes 72 such that the solidifying substance does not cover one or more of the electrodes. In some embodiments, lead 68 may include exit ports 74 at the proximal side of electrodes 72 as well as exit ports 66 (shown in FIG. 4A) at the distal side of electrodes 72. In this manner, lead 68 may be secured at two separate locations to prevent lead migration.

FIG. 4C shows lead 76, which includes lead body 78, electrodes 80, and exit ports 82, 84, 86, 88, and 90. Lead body 78 includes multiple exit ports at locations throughout the axial length and circumference of lead body 78 to strongly secure lead 76 to adjacent tissue. Exit ports 82 are located proximal to electrodes 80 and exit ports 90 are located distal to electrodes 80. In addition, exit ports 84, 86, and 88 are located between electrodes 80. This arrangement of exit ports 82, 84, 86, 88, and 90 for delivering the solidifying substance may be beneficial where close proximity electrode-tissue placement is vital to the efficacy of the therapy.

In alternative embodiments, exit ports may be placed at any location on the outer surface of lead body 78. For example, exit ports may be present at much more proximal locations along lead body 78 (i.e., at axial locations between the axial location of exit holes 82 and the proximal end of lead body 78, which is not shown in FIG. 4C) to secure lead 76 at certain bends or tissues within patient 16. In addition, exit ports 82-88 may have a shape different than a circle. For example, ovals, squares, triangles, or irregular shapes may be used to present the solidifying substance to surrounding tissue. These shapes may direct the solidifying substance in a certain direction with respect to lead 76, such as toward a distal, proximal, or radially outward direction.

Figure 5A:
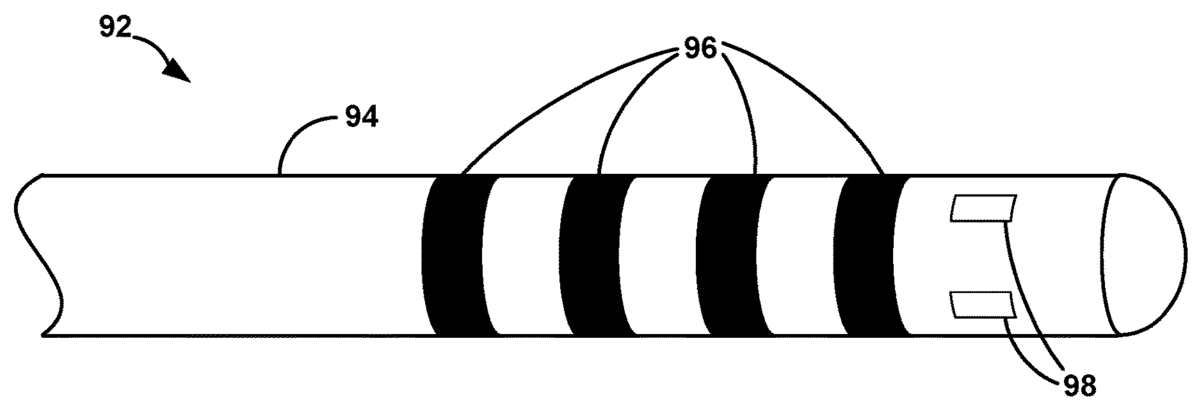
FIGS. 5A-5B are perspective drawings illustrating exemplary leads with exit ports of varying shapes and sizes.
Figure 5B:
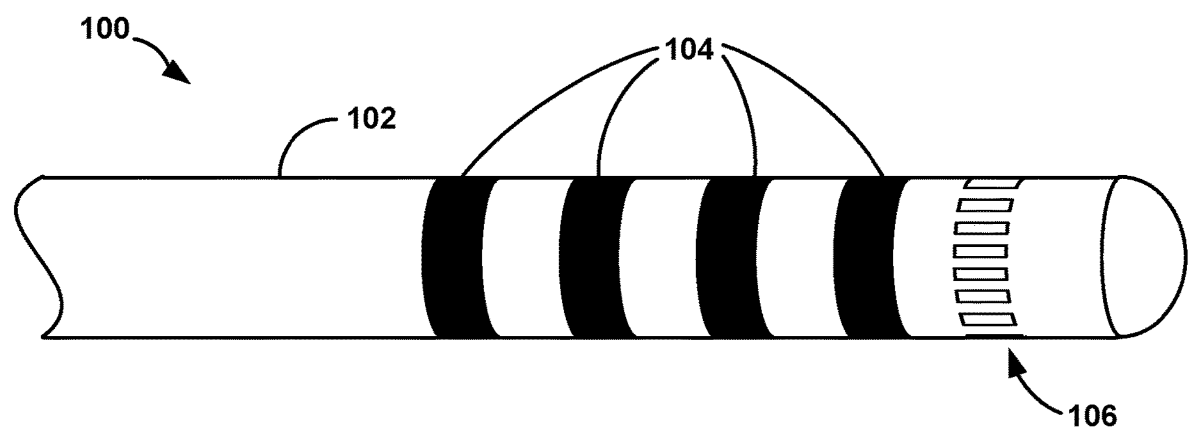

FIGS. 5A-5B are perspective drawings illustrating exemplary leads with exit ports of varying shapes and sizes. As shown in FIG. 5A, lead 92 includes lead body 94, electrodes 96, and exit ports 98. Exit ports 98 are located distal to electrodes 96 and are rectangular in shape. The rectangular exit ports 98 may allow a greater surface area of tissue to be contacted by the adhesive or other solidifying substance. In other embodiments, the rectangular exit ports 98 may be located anywhere on the longitudinal outer surface of lead body 94, such as the different locations for exit ports shown in FIGS. 4A-4C.

FIG. 5B illustrates lead 100 that includes lead body 102, electrodes 104, and exit ports 106. Exit ports 106 are located distal to electrodes 104, but in other embodiments, the exit ports may be located at any location along the longitudinal outer surface of lead body 102. Lead body 102, and in particular, a longitudinal surface of lead body 102 defines a plurality of relatively small, rectangular exit ports 106 that arranged in a ring around the circumference of lead body 102. In this manner, the solidifying substance is presented to the tissue in a ring-like manner to secure lead 100 to the tissue completely around the circumference of lead body 102 at that axial location. In embodiments in which the solidifying substance includes two fluids that combine to create the adhesive, the two fluids may flow out of alternating exit ports to create the adhesive ring around the distal end of lead 100.

The arrangement of exit ports 106 around an outer circumference of lead body 102 creates a relatively large surface area for the solidifying substance to flow out into the lead-tissue interface area, thereby providing a relatively large area for fixing lead 100 to surrounding tissue. In alternative embodiments, exit ports 106 may be replaced with many smaller holes or a mesh component that allows a larger quantity of solidifying substance to be released by lead 100. In addition, exit ports 106 may be located at locations proximate to electrodes 104 or in between electrodes 104. In some embodiments, different types of exit ports described in FIGS. 4A-4C and FIGS. 5A-5B may be combined to create one lead with different exit port combinations and/or arrangements.

Figure 6A:
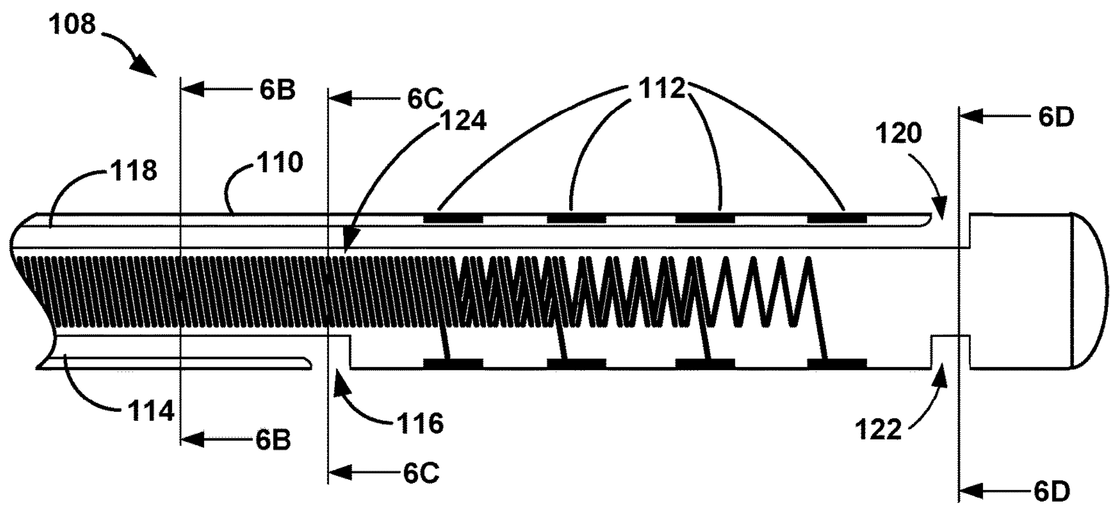
FIGS. 6A-6D are cross-sectional views of an exemplary lead with conduits leading to multiple circumferential exit ports.

FIGS. 6A-6D are cross-sectional views of an exemplary lead with conduits leading to multiple circumferential exit ports. Lead 108 may represent the cross-sectional views of any of leads 60, 68, 76, 92 or 100. As shown in FIG. 6A, lead 108 includes lead body 110, electrodes 112, conduit 114, exit port 116, conduit 118, exit ports 120 and 122, and coiled conductor 124. Lead 108 further includes a plurality of other exit ports 128, 130, 132, 136, and 138, which can be seen in the cross-sectional views of lead 108 shown in FIGS. 6C and 6D. Electrodes 112 are ring electrodes disposed on the outer surface of lead body 110 and are electrically connected to coiled conductor 124. In particular, each electrode 112 is electrically connected to a wire of coiled conductor 124, and each wire may spin off from the coiled conductor at any location around the circumference of lead 108 to allow conduits (e.g., conduits 114 and 118) to pass to the distal portion of lead body 110. In some embodiments, coiled conductor 124 may not be in a coiled configuration.

Lead 108 includes exit port 116, 128, 130, and 132 located proximally to electrodes 112 and exit ports 120, 122, 136, and 138 located distally to electrodes 112. Exit ports 116, 128, 130, and 132 are in fluidic communication with conduit 114 while exit ports 120, 122, 136, and 138 are in fluidic communication with conduit 118. Conduits 114 and 118 each generally run parallel to longitudinal outer surface 110A (shown in FIG. 6B) of lead body 110. However, at the axial location of the respective exit ports 116, 120, 122, 128, 130, 132, 136, and 138 for each conduit 114 and 118, each conduit 114 and 118 has a portion that extends in a generally radial direction to deliver the solidifying substance to each of the associated exit ports. For example, as shown in FIG. 6C, conduit 114 defines semi-annular, radially-extending portion 126 that fluidically connects each exit port 116, 128, 130, and 132. Alternatively, each conduit 114 and 118 has a ring-shaped portion that extends within lead body 110 to deliver the solidifying substance to each of the associated exit ports 116, 120, 122, 128, 130, 132, 136, and 138. In this manner, one conduit is only needed for each axial position of exit ports.

Each conduit 114 and 118 has a central longitudinal axis that is different than the central longitudinal axis of coiled conductor 124. For example, in the embodiment shown in FIGS. 6A-6D, conduit 114 has a central longitudinal axis 114A (shown FIG. 6B) that is different than central longitudinal axis 118A (shown FIG. 6B) of conduit 118 and central longitudinal axis 110B (shown FIG. 6B) of lead body 110. Longitudinal axes 114A, 118A, and 110B run substantially perpendicular to the plane of the image of FIG. 6B.

In other embodiments, conduits 114 and 118 may have other arrangements with respect to lead body 110. For example, in one embodiment, conduit 114 and/or conduit 118 may be located outside of lead body 110. In another embodiment, conduit 114 and 118 may not be located outside of coil conductor 124. For example, conduit 118 may reside within coiled conductor 124 and share a common central axis to lead body 110 while conduit 114 remains outside of coiled conductor 124. Alternatively, both conduits 114 and 118 may reside within coiled conductor 124, which may be disposed near the longitudinal outer surface 110A of lead body 110. In any case, each conduit 114 and 118 delivers the solidifying substance to an annular ring connecting one or more exit ports at the same axial position.

Figure 6B:
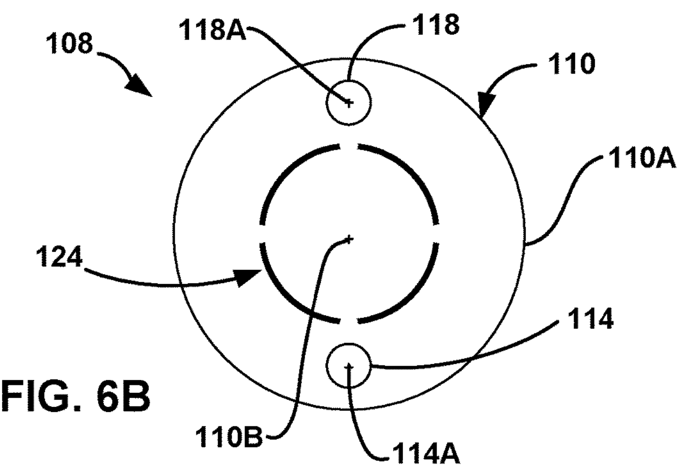
Figure 6C:
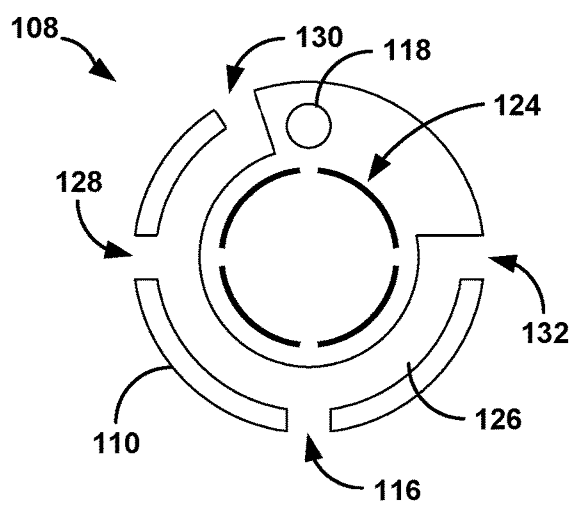

FIG. 6B shows a cross-section of lead 108 taken along line 6B-6B in FIG. 6A, which represents the cross-section of lead 108 proximal to the location of any exit ports 116, 120, and 122. Lead 108 includes lead body 110, coiled conductor 124, and conduits 114 and 118. While conduits 114 and 118 are shown to be oriented 180 degrees away from each other (i.e., on opposite sides of coil conductor 124), conduits 114 and 118 may be located at any circumferential position outside of coiled connector 124 in other embodiments.

FIG. 6C shows the cross-section of lead 108 taken along line 6C-6C in FIG. 6A, which is located at the axial position of the proximal exit port 116 of associated conduit 114. Lead 108 includes lead body 110 surrounding coiled conductor 124, conduit 118, which includes a semi-annular portion 126 at the end of conduit 114. Semi-annular portion 126 fluidically couples all exit ports 116, 128, 130 and 132 located around the outer circumference of lead body 110. As the solidifying substance is delivered through conduit 114, the substance reaches semi-annular portion 126 and exits exit ports 116, 128, 130, and 132 at approximately the same time. Exit port 130 is not located 90 degrees from the closest exit ports 128 or 132 because conduit 118 passes through lead body 110 at that location. However, other embodiments may include exit ports 128, 132 and 116 rotated around the circumference of lead body 110 to allow all exit ports 116, 128, 130 and 132 to remain equidistant from each other.

Figure 6D:
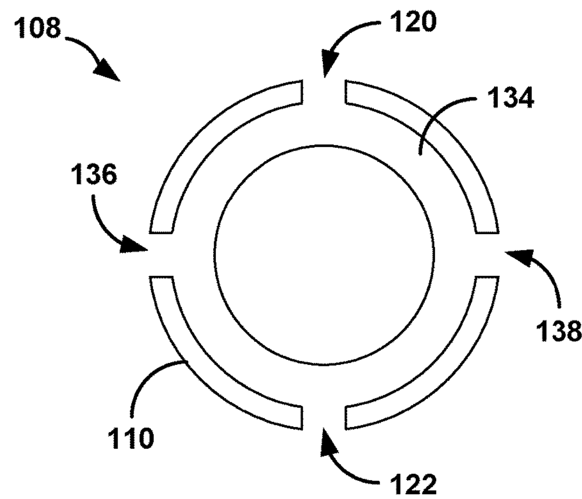

FIG. 6D displays the cross-section of lead 108 at line 6D-6D in FIG. 6A, which is at the axial position of exit ports 120, 122, 136 and 138. Lead 108 is shown to include annular portion 134 located within lead body 110 and in fluidic communication with exit ports 120, 122, 136, and 138. Conduit 118 terminates at annular portion 134, thereby allowing conduit 118 to supply exit ports 120, 122, 136, and 138 with the solidifying substance that secures lead 108 within the surrounding tissue. Since coiled conductor 124 is no longer present at the axial location of annular portion 134 of conduit 118, in some embodiments, annular portion 134 may be a disk-shaped void within lead body 110 that connects all exit ports 120, 122, 136, and 138.

As shown, lead 108 is constructed to utilize a solidifying substance that cures in the presence of moisture. However, lead 108 may be modified to contain the necessary conduits to deliver two or more fluids that cure upon contact with each other. Furthermore, the size, shape, location, and number of exit ports 116, 120, 122, 128, 132, 136, and 138 in FIGS. 6A-6D are merely exemplary. In other embodiments, lead 108 may include a fewer or greater number of exit ports to deliver the solidifying substance to the surrounding tissue. For example, lead 108 may also include a conduit including a semi-annular portion to deliver a solidifying substance to exit ports located between electrodes 112. In some embodiments, lead body 110 may have a cross-sectional shape other than a circle. For example, the radius of lead body 110 may be larger where a conduit is present in order to accommodate the conduit. Accordingly, in regions where a conduit is not present in lead body 110, lead body 110 may have a smaller radius and the longitudinal outer surface 110A of lead body 110 can reside closer to center longitudinal axis 110B of lead body 110.

In alternative embodiments of lead 108, conduits 114 and 118 may not be generally cylindrical. For example, conduit 114 or 118, or both, may be constructed with a semi-annular shape that is capable of flowing the necessary volume of solidifying solution out of the respective exit ports into the tissue while reducing the overall profile of lead 108. Such a modification to conduits 114 and 118 may be necessary desirable to reduce a profile of lead 140, which may be helpful for situations in which the anatomy of the patient provides a limited area for lead 140 to be introduced into or through to reach the target tissue site. In addition, in one embodiment, conduits 114 and 118 are each formed of a collapsible material. That is, conduits 114 and 118 may be in a substantially collapsed when a solidifying substance is not within conduits 114 and 118, but when the solidifying substance is flowing through the respective conduit 114 and 118, conduits 114 and 118 expand to accommodate the solidifying substance. Collapsible conduits 114 and 118 may enable conduits 114 and 118, and in some case, lead 108, to retain a relatively small profile when no substance is flowing through conduits 114 and 118. These characteristics as well as other shapes of conduits 114 and 118 are contemplated herein.

While lead 108 is constructed so that all exit ports present the solidifying substance to the tissue of the patient, the clinician may decide to limit the locations where lead 108 is secured to the tissue. For example, the clinician may only supply the solidifying substance to conduit 114 and secure lead 108 proximal to electrodes 112 via exit ports 116, 128, 130 and 132. Alternatively, the clinician may only supply the solidifying substance to conduit 118 to secure lead 108 at the distal portion of the lead. The selective use of conduits 114 and 118 may enable the clinician to accommodate fixation of lead 108 to various anatomical configurations of the patient proximate to the target tissue site.

Figure 7A:
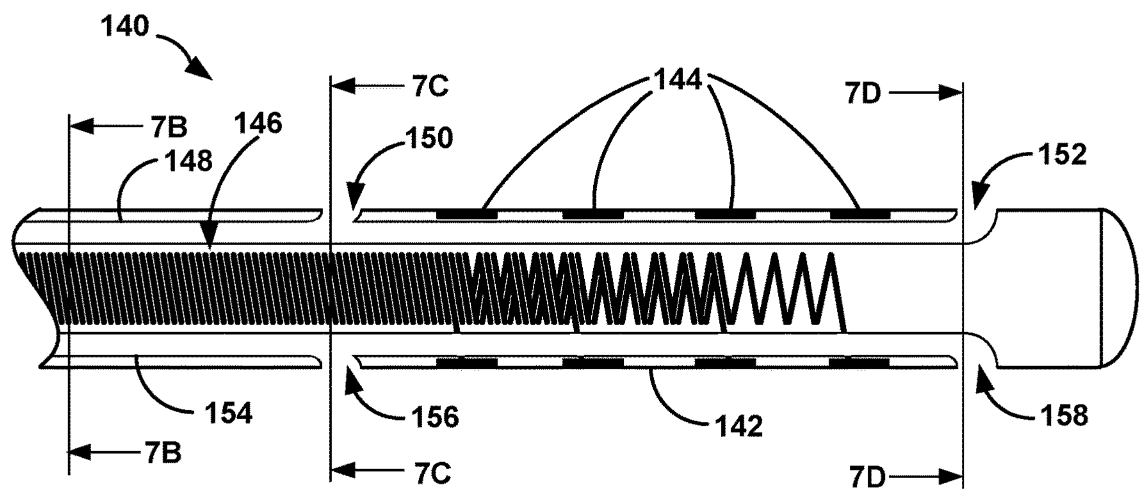
FIGS. 7A-7D are cross-sectional views of an exemplary lead with conduits leading to multiple longitudinal exit ports.

FIGS. 7A-7D are cross-sectional views of an exemplary lead with conduits each leading to multiple longitudinal exit ports along the longitudinal direction of the lead. Lead 140 is an embodiment of lead 14 and may represent the cross-sections of any of leads 60, 68, 76, 92 or 100. As shown in FIG. 7A, lead 140 includes lead body 142, electrodes 144, coiled conductor 146, conduit 148, exit ports 150 and 152, conduit 154, exit ports 156 and 158. Lead 140 further includes conduits 160 and 162 (shown in FIGS. 7C and 7D) and lead body 142 further defines exit ports 166, 170, 174, and 178 (shown in FIGS. 7C and 7D). Electrodes 144 are ring electrodes disposed on the longitudinal outer surface 142A (FIG. 7B) of lead body 142 and electrically connected to coiled conductor 146. In particular, each electrode 144 is electrically connected to a wire of coiled conductor 146, and each wire may leave the coiled conductor at any location around the circumference of lead body 142 to allow conduits to pass to the distal portion of lead body 142. In some embodiments, coiled conductor 146 may not in a coiled arrangement.

Lead 140 includes exit ports located proximally to and distally from electrodes 144, similarly to lead 108. In particular, exit ports 150, 156, 166, and 170 are located proximal to electrodes 144, while exit ports 152, 158, 174, and 178 are located distal to electrodes 144.

Each conduit 148, 154, 160, and 162 is in fluidic communication with at least two exit ports and delivers a solidifying substance to the respective exit ports. In the embodiment shown in FIGS. 7A-7D, exit ports 150 and 152 are in fluidic communication with conduit 148, exit ports 156 and 158 are in fluidic communication with conduit 154, exit ports 170 and 178 are in fluidic communication with conduit 160, and exit ports 166 and 174 are in fluidic communication with conduit 162. Thus, conduits 148, 154, 160, and 162 are each configured to deliver the solidifying substance to exit ports located on either side of electrodes 144 and at the same circumferential position on lead body 142. Conduits 148, 154, 160, and 162 each extend generally parallel to lead body 142 and the central axes of each of conduits 148, 154, 160, and 162 are unaligned with each other as well as with the central axis of coiled conductor 146. In this manner each conduit 148, 154, 160, and 162 only delivers the solidifying substance to an exit port located at the same general circumferential position as the respective conduit 148, 154, 160, and 162.

While conduits 148, 154, 160, and 162 are located outside of coiled conductor 146, other embodiments may employ different construction. For example, conduit 148 may reside within coiled conductor 146 and share a common central axis with lead body 142 while conduits 154, 160, and 162 remain outside of coiled conductor 146. Alternatively, all four conduits 148, 154, 160, and 162 may reside within a coiled conductor 146 that is disposed near the surface of lead body 142. In any case, each conduit 148, 154, 160, and 162 delivers the solidifying substance to one or more exit ports at the same generally circumferential position. It may be necessary for coiled conductor 146 to separate and provide an opening to exit ports 150 and 156 from any conduits that reside within the coiled conductor.

Figure 7B:
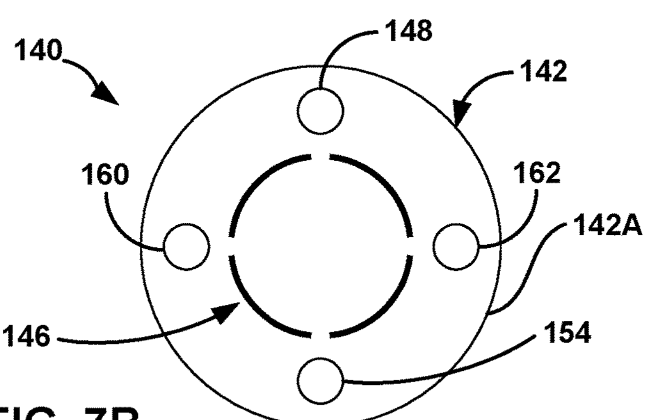

FIG. 7B shows a cross-sectional view of lead 140 taken along line 7B-7B in FIG. 7A, which is proximal to the location of any exit ports. Lead 140 includes lead body 142, coiled conductor 146, and conduits 148, 154, 160 and 162. While conduits 148, 154, 160 and 162 are shown to be oriented 90 degrees with respect to each other, the conduits may be located at any circumferential position outside of coiled connector 146 in other embodiments. Alternatively, lead 140 may include more or less than four conduits to match the desired number of exit ports around the circumference of lead body 142. In some embodiments, conduits 148, 154, 160 and 162 may be helical in shape within lead body 142 to promote lead 140 flexibility, where the circumferential location of each conduit and corresponding exit port changes with axial position in the lead.

Figure 7C:
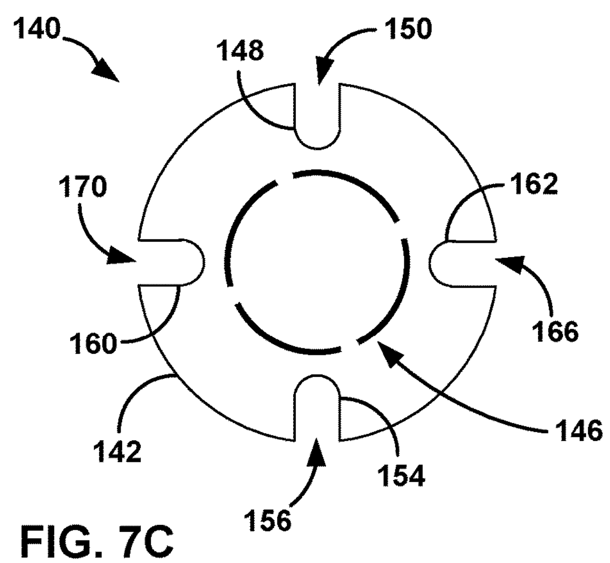

FIG. 7C shows the cross-sectional view of lead 140 taken along line 7C-7C in FIG. 7A, which is at the axial position of the proximal exit ports 150, 156, 166, and 170. Lead 140 includes lead body 142 surrounding coiled conductor 146, conduits 148, 154, 160, and 162 with corresponding exit ports 150, 156, 170, and 166, respectively. As the solidifying substance is delivered via each conduit 148, 154, 160, and 162, the solidifying substance leaves each respective exit port as the substance proceeds to the distal end of lead 140. As mentioned above, conduits and exit ports may be located any circumferential position of lead 140.

Figure 7D:
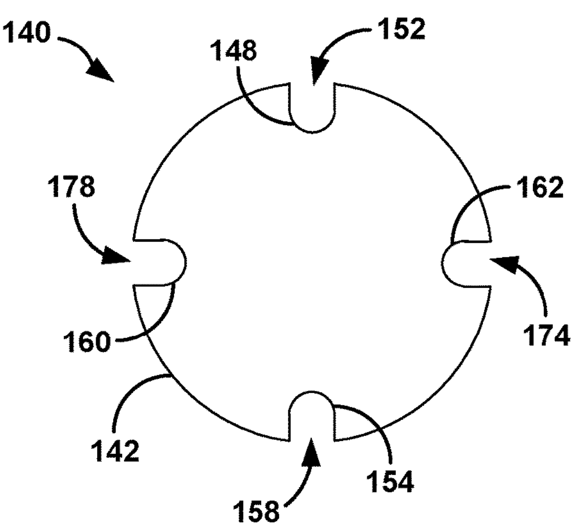

FIG. 7D displays the cross-sectional view of lead 140 taken along line 7D-7D in FIG. 7A, which is at the axial position of exit ports 152, 158, 174, and 178 which are located at the distal terminating end of conduits 148, 154, 162, and 160, respectively. In some embodiments, exit ports 152, 158, 174, and 178 may each have a smaller cross-sectional area than proximal exit ports 150, 156, 166, and 170. This difference in exit port cross-sectional area may help ensure that the solidifying substance exits at proximal locations instead of all flowing out of each conduit at the distal location. Alternatively, each conduit may gradually be reduced in diameter from a proximal end of lead 140 to a distal end.

As shown, lead 140 is constructed to utilize a solidifying substance that cures in the presence of moisture. However, lead 140 may be modified to contain the necessary conduits to deliver two or more fluids that cure upon combining together. In other embodiments, lead 140 may include a fewer or greater number of exit ports to present the solidifying substance to the tissue. For example, more conduits may fill the region between the longitudinal outer surface 142A (FIG. 7B) of lead body 142 and coiled conductor 146. In some embodiments, lead body 142 may have a noncircular cross-sectional shape. For example, as described above with respect to lead 108 of FIGS. 6A-6D, the radius of lead body 142 may have a larger profile (or radius) where a conduit is present in order to accommodate the conduit and lead body 142 may have a relatively smaller profile in regions that do not include a conduit.

In alternative embodiments of lead 140, conduits 114 and 118 may not be generally cylindrical. For example, conduits 148, 162, 154 and 160 may be constructed with a semi-annular shape that is capable of flowing the necessary volume of solidifying solution out of exit ports into the tissue while reducing the radius of lead 140. Such a modification to the conduits may be desirable to reduce a profile of lead 140, which may be helpful for situations in which the anatomy of the patient provides a limited area for lead 140 to be introduced into or through to reach the target tissue site. In addition, as discussed above with respect to conduits 114 and 118 in FIGS. 6A-6D, conduits 148, 162, 154 and 160 may be collapsible to allow expansion when the solidifying substance is flowing and remain small in diameter when no substance is flowing. These and other shapes of conduits 148, 162, 154 and 160 are contemplated herein.

While lead 140 is constructed so that all exit ports present the solidifying substance to the tissue of the patient, the clinician may decide to limit the locations where lead 140 is secured to the tissue. For example, the clinician may only supply the solidifying substance to conduit 148 and secure lead 140 proximal to electrodes 144 via exit ports 150 and 152. Alternatively, the clinician may supply the solidifying substance to conduits 148 and 162 to secure lead 140 one a greater surface of one side of the lead. In situations where the stimulation field is desired in only one circumferential direction from lead 140, such as the sides which include conduits 160 and 154, the solidifying substance may be delivered to conduits 148 and 162 that include exit ports in between electrodes 144. This may help prevent the solidifying substance from effectively covering the portions of electrodes 144 on the sides of conduits 148 and 162, which may interfere with electrical stimulation to the tissues adjacent that area of lead 140. However, the solidifying substance may include conductive particles in some embodiments which prevent the solidifying substance that covers any portion of electrodes 144 to inhibit electrical stimulation.

Figure 8:
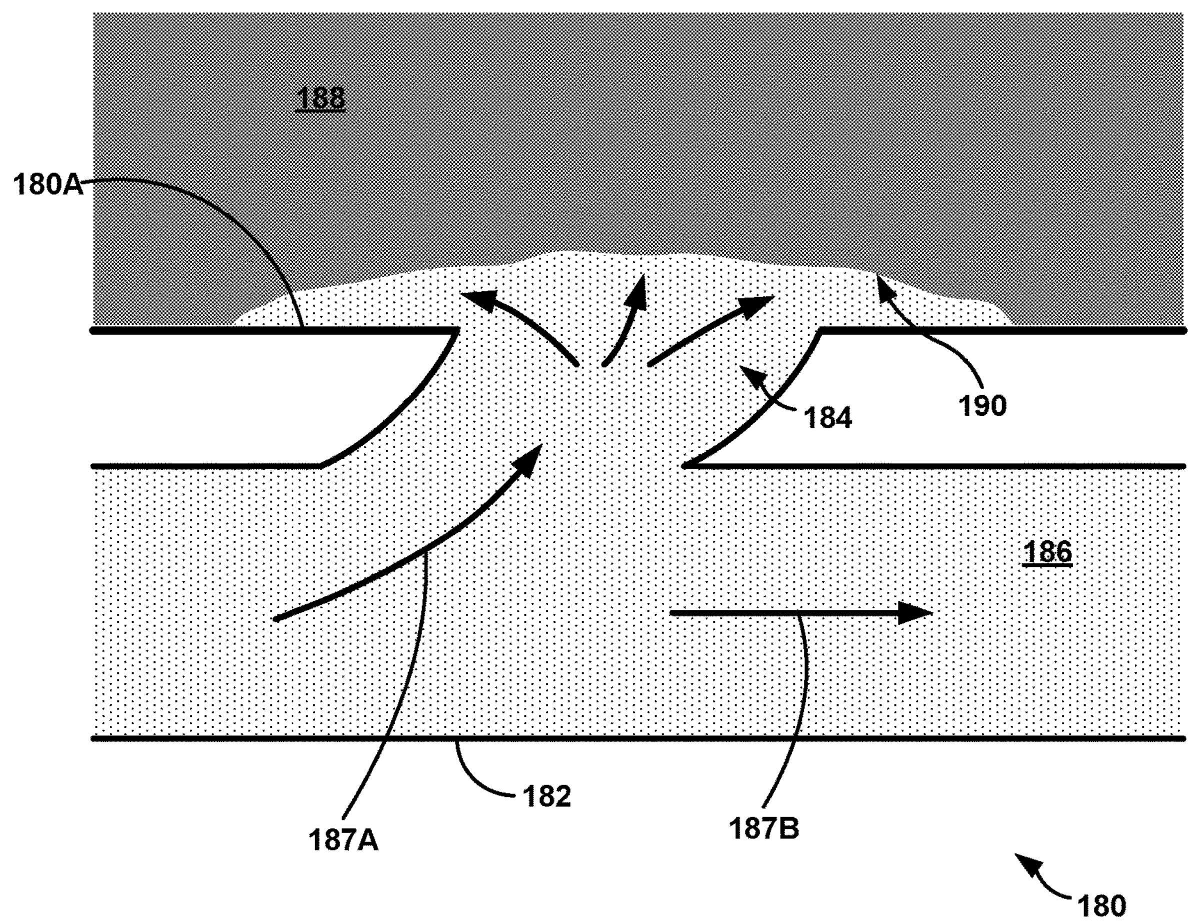
FIG. 8 is a conceptual illustration of exemplary flow of an adhesive from the lead into the surrounding tissue.

FIG. 8 is a schematic cross-sectional view of a part of lead 180, which includes conduit 182 and defines exit port 184. FIG. 8 provides a conceptual illustration of exemplary flow of solidifying substance 186 from conduit 182, through exit port 184, and into surrounding tissue 188. Lead 180 has been implanted in tissue 188, which may be, for example, tissue near target stimulation site 18 in FIG. 1A, near occipital region 29 in FIG. 1B or proximate to any other therapy delivery site in a patient. Lead 180 may be an embodiment of any leads 14, 60, 68, 76, 92, 100, 108 or 140.

Solidifying substance 186 is introduced into conduit 182 near a proximal end of lead 180 and flows from the proximal end of lead 180 toward the distal end of lead 180 in a direction indicated by arrows 187A and 187B. As the flow of solidifying substance 186 passes exit port 184, some solidifying substance 186 flows toward and out exit port 184, as indicated by arrow 187A, while some solidifying substance 186 continues flowing toward the distal end of lead 180, as indicated by arrow 187B. Once solidifying substance 186 leaves exit port 184, the substance 186 contacts adjacent tissue 188 at adhesion interface 190. The water from tissue 188 activates solidifying substance 186 and causes the substance 186 to cure and adhere to outer surface 180A of lead 180 and tissue 188. In this manner, lead 180 is attached to tissue 188 around the vicinity of exit port 184, which helps to prevent migration of lead 180 following implantation in tissue 188.

While FIG. 8 displays a solidifying substance that is cured from added moisture, in another embodiment, solidifying substance 186 may include two fluids that flow down two conduits and combine at exit port 184 as they both flow into the surrounding tissue 188. The combination of the two fluids at adhesion interface 190 causes tissue 188 to adhere to lead 180. Alternatively, an energy curable solidifying substance may be delivered to tissue 188 and cured via energy from the tissue or another external energy source. For example, conductive heat may activate solidifying substance 186. An energy may also be used to deactivate solidifying substance 186 when lead 180 is to be removed from patient 16.

Figure 9:
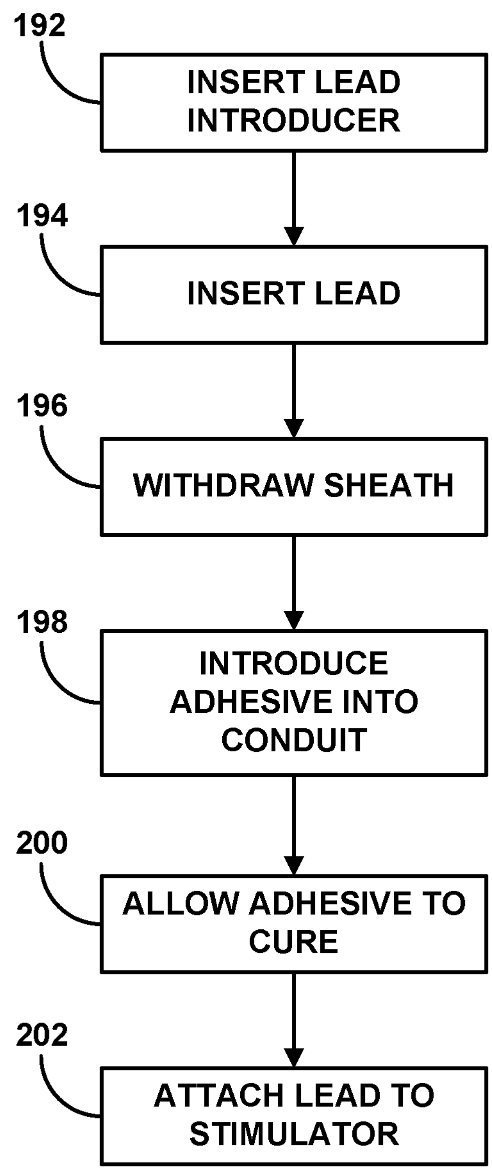
FIG. 9 is a flow diagram illustrating an exemplary process for securing a lead to a tissue of a patient using an adhesive delivered by the lead.

FIG. 9 is a flow diagram illustrating an exemplary process for securing a lead to a tissue of a patient using an adhesive delivered by the lead. While lead 60 is referenced in the description of the process for securing a lead in accordance with the process shown in FIG. 9, a clinician may implant any of leads 14, 60, 68, 76, 92, 100, 108 or 140 described herein in accordance with the process shown in FIG. 9. First, the clinician inserts a lead introducer into patient 16 proximate to the target tissue site (192). The tissue site may be adjacent to the sacral nerve, occipital nerve, or any other nerve which may provide effective therapy to patient 16, or alternatively, adjacent to any other therapy deliver site. For example, in some therapy programs, electrodes 64 of lead 60 may be positioned proximate to a general region of patient-reported pain. Next, the clinician inserts lead 60 into the lead introducer until the electrodes of the lead are placed correctly (194). The clinician next removes the lead introducer and sheath that separates lead 60 from the surrounding tissue (196).

After the clinician has removed the sheath, the clinician attaches a supply of solidifying substance, or adhesive, and introduces (e.g., injects) the adhesive into the one or more conduits of lead 60. After the solidifying substance flows through the conduit(s) and exits the conduit(s) through exit ports 66, the solidifying substance contacts the tissue adjacent to exit ports 66 near the distal end of the lead 60 (198). The clinician waits a predetermined amount of time until the adhesive is cured or until the clinician can determine independently that the adhesive is cured, e.g., the clinician may pull slightly on lead 60 to identify if the lead is secure (200). Once a distal portion of lead 60 is securely fixed to tissue near the target therapy delivery site, the clinician can tunnel a proximal portion of lead 60 (or a lead extension to which the lead 60 is attached) to the location of the implanted neurostimulator 12 and electrically and mechanically couple the lead to the neurostimulator (202).

Figure 10A:
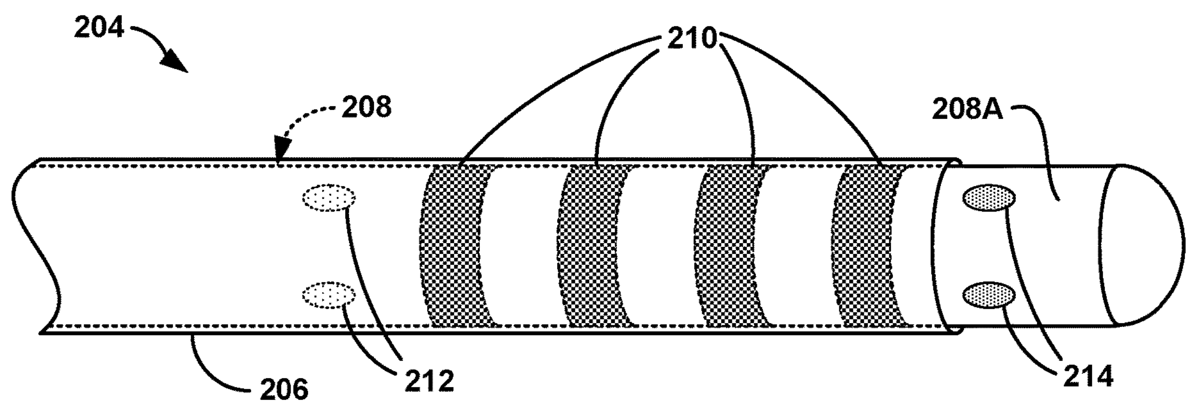
FIGS. 10A-10C are perspective drawings illustrating exemplary leads with adhesive elements that are activated by moisture.
Figure 10B:
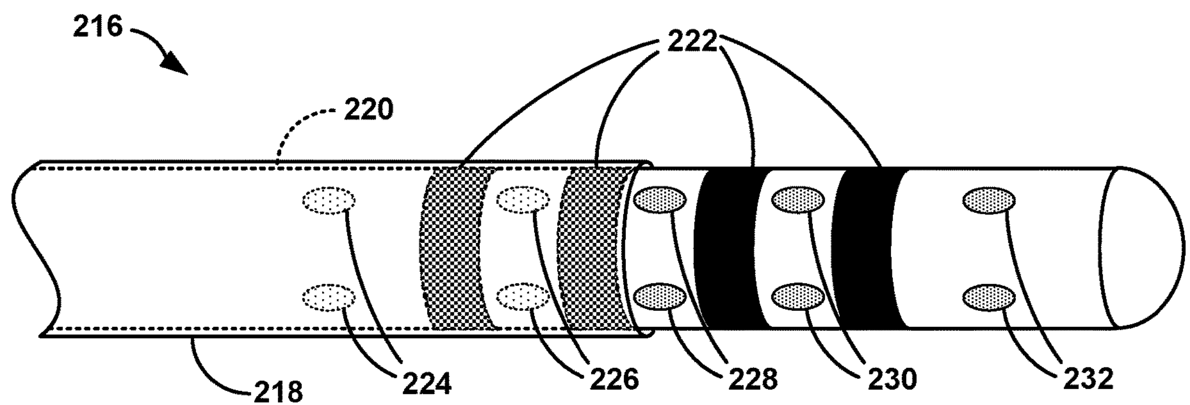
Figure 10C:
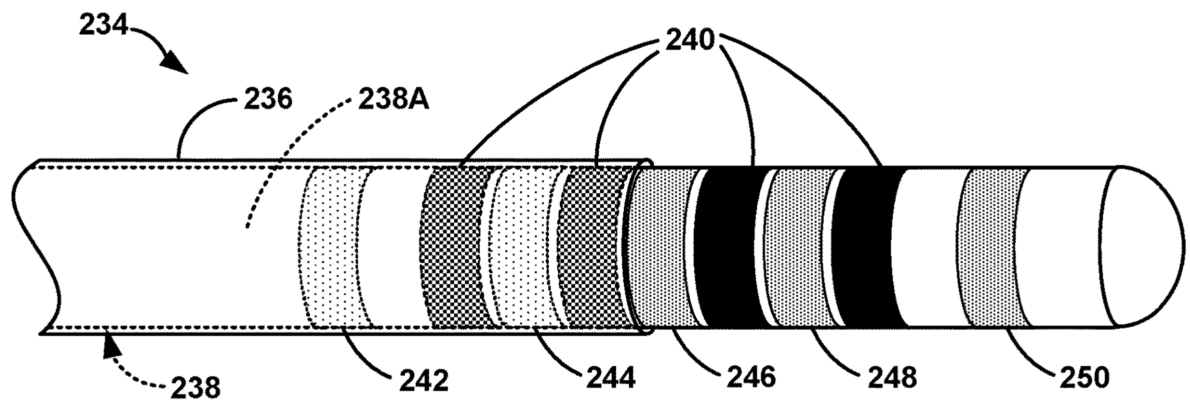

FIGS. 10A-10C are perspective drawings illustrating exemplary leads with adhesive elements that are activated by moisture, heat or other characteristics of the implantation environment. Lead 204 is an embodiment of lead 14 of FIGS. 1A-2. The distal portion of lead 204 is shown in FIG. 10A, which includes lead body 208 (partially shown in phantom lines), electrodes 210, and adhesive elements 212 and 214. The distal end of sheath 206 is also shown. Sheath 206 may be used to cover electrodes 210 and adhesive elements 212 and 214 until lead 204 has been implanted at the target tissue site within patient 16. Sheath 206 may separate adhesive elements 212 and 214 from surrounding tissue until lead 204 reaches the target tissue site in order to help prevent premature activation of adhesive elements 212 and 214. Once lead 204 is correctly positioned by the clinician, the clinician removes sheath 206 from lead body 208 to expose electrodes 210 and adhesive elements 212 and 214 to the surrounding tissue. In FIG. 10A, Sheath 206 is shown to be partially removed to expose adhesive elements 214 at the distal end of lead 204.

Lead 204 may also include adhesive elements that are similar to adhesive elements 212 and 214 on the opposite side of lead body 208 (not shown). Each adhesive element 212 and 214 is disposed on longitudinal outer surface 208A of lead body 208 and includes an adhesive that is pre-bonded to the lead body and inactive or otherwise not bonded to sheath 206. Each adhesive elements 212 and 214 may each protrude (in a radial direction) slightly from longitudinal outer surface 208A of lead body 208. Alternatively, adhesive elements 212 and 214 may be disposed in a recess of the lead body such that each adhesive element is flush with longitudinal outer surface 208A of lead body 208 or adhesive elements 212 and 214 may be embedded in longitudinal outer surface 208A lead body 208. Alternatively, adhesive elements 212 and 214 may be deposited on outer source 208, e.g., as beads of adhesive material.

The adhesive forming adhesive elements 212 and 214 may be 2-octyl cyanoacrylate, fibrin glue, or any other type of substance that cures upon contact with water or another fluid present in the surround tissue at the implant site. In addition, the solidifying substance may be activated or cured from body heat or an electrical current delivered to the substance. Once sheath 206 is pulled toward the proximal side of lead 204 and to expose adhesive elements 212 and 214, water from the adjacent tissue contacts the adhesive material and activates that adhesive. In this way, the clinician may "activate" adhesive elements 212 and 214 by withdrawing sheath 206. The activated adhesive begins to adhere to the adjacent tissue and cure until the adhesive is bonded between the lead and the tissue to secure lead 204 and keep electrodes 210 proximal to the target tissue site. In other embodiments, adhesive elements 212 and 214 may have a shape other than circles.

In the embodiment shown in FIG. 10A, adhesive elements 212 and 214 do not require any additional energy or mechanism to activate adhesive elements 212 and 214, and adhesive elements 212 and 214 may be used alone or in combination with other fixation elements to secure lead 204 within patient 16. Additional fixation elements may be any suitable actively or passively deployed fixation element that helps prevent migration of lead 204 when lead 204 is implanted in the patient, such as, but not limited to, one or more tines, barbs, hooks, wire-like elements, balloon-like fixation elements, pinning fixation elements, collapsible or expandable fixation structures, and so forth. The fixation elements may be composed of any suitable biocompatible material, including, but not limited to, polymers, titanium, stainless steel, Nitinol, other shape memory materials, hydrogel or combinations thereof.

In other embodiments, lead 204 may include any suitable number of adhesive elements in any suitable arrangement about lead body 208. Another example of a lead including adhesive elements is shown in FIG. 10B.

FIG. 10B shows lead 216, which includes lead body 220 (partially shown in phantom lines), electrodes 222, and adhesive elements 224, 226, 228, 230 and 232. Adhesive elements 224 are disposed proximal to electrodes 222 while adhesive elements 232 are disposed distal to the electrodes, which is a similar arrangement as adhesive elements 212 and 214 of lead 204. Adhesive elements 226, 228 and 230 are disposed between each electrode 222. Adhesive elements 226, 228 and 230 bond lead 216 to the target tissue close to electrodes 222, thereby minimizing the distance between electrodes 222 and the target tissue during the duration of stimulation therapy. Alternatively, any number of adhesive elements may be disposed on any longitudinal outer surface of lead body 220. In addition, adhesive elements may not need to be of uniform shapes and sizes to customize lead 216 for implantation at any tissue site.

Sheath 218 is configured to receive lead body 220 and sized to cover adhesive elements 224, 226, 228, 230, and 232 until lead 216 is correctly placed within patient 16.

In the view shown in FIG. 10B, sheath 218 has been partially withdrawn to expose adhesive elements 228, 230 and 232.

FIG. 10C illustrates another embodiment of a lead including adhesive elements disposed about a longitudinal outer surface of the lead. In particular, FIG. 10C shows a perspective view of lead 234, which includes lead body 238, electrodes 240 at the distal end of lead body 238 (partially shown in phantom lines), and adhesive elements 242, 244, 246, 248 and 250. Sheath 236 is sized to covers a majority of the length of longitudinal outer surface 238A of lead body 238; however, sheath 236 is shown to be partially removed from lead 234 in FIG. 10C.

Adhesive elements 242, 244, 246, 248 and 250 are activated by surrounding moisture from tissue to bond lead 234 to the tissue. Adhesive elements 242 and 250 are shown on the proximal and distal sides of electrodes 240, respectfully, and adhesive elements 244, 246 and 248 are disposed between the four electrodes. Adhesive elements 242-250 are shaped as annular rings that extend around the entire outer circumference of lead body 238. In this manner, adhesive elements 242-250 may each cover a relatively large surface area of longitudinal outer surface 238A of lead body 238 as compared to adhesive elements 212 and 214 of FIG. 10A in order to maximize the bond between lead body 238 and adjacent tissue. In alternative embodiments, a lesser or greater portion (e.g., an entire portion) of lead body 238 may be covered with one or more adhesive element to secure lead 234. A greater adhesive surface area may be desirable in cases where lead 234 is implanted proximate to a region of patient 16 that is subject to large or frequent movements.

Figure 11:
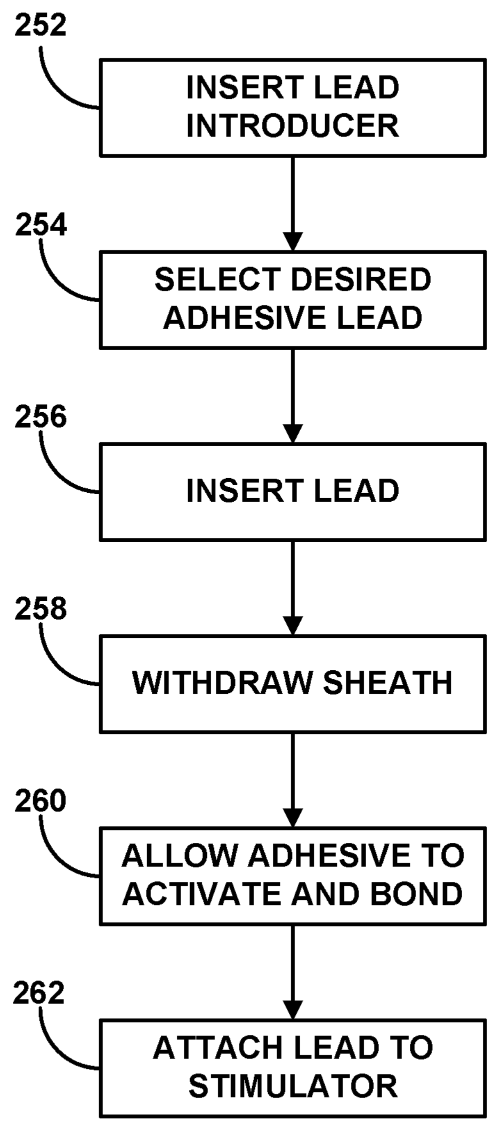
FIG. 11 is a flow diagram illustrating an exemplary process for securing a lead to a tissue of a patient using an adhesive element.

FIG. 11 is a flow diagram illustrating an exemplary process for securing a lead to a tissue of a patient using an adhesive element. A clinician may implant any of leads 14, 204, 216 or 234 in accordance with the process shown in FIG. 11. However, lead 204 will be referenced as an example. First, the clinician inserts a lead introducer into patient 16 proximate to the target tissue site (252). The tissue site may be adjacent to the sacral nerve, occipital nerve, any other nerve which may provide effective therapy to patient 16 or adjacent to any other suitable therapy deliver site. Next, the clinician selects the appropriate lead with adhesive elements positioned to best secure the lead without damaging tissue (254). For example, the clinician may select a lead including adhesive elements 212 and 214 that are arranged about lead body 208 in a manner that accommodates adhesion of lead body 208 to a specific anatomical region of patient 16. The clinician then inserts lead 204 into the lead introducer until electrodes 210 of lead 204 are placed correctly in proximity to the target stimulation site (256).

The clinician next removes the lead introducer and sheath 206 that covers lead 204 from the surrounding tissue (258). Once sheath 206 has been withdrawn from lead body 208 to expose adhesive elements 212 and 214, adhesive elements 214 and 216 become activated and bond to the surrounding tissue. The clinician may wait to allow adhesive elements 212 and 214 to sufficiently bond to the surrounding tissue (260). Once lead 204 is secure, the clinician may attach the proximal end of lead 204 to neurostimulator 12 (262).

In some embodiments, the clinician may remove sheath 208 in segments to slowly adhere one or more adhesive elements at a time during implantation. This method may be beneficial when implanting a lead with multiple curves or complex adhesion locations along the length of the lead. In other embodiments, the adhesive elements may begin to adhere slowly because the activation in response to moisture may take several minutes or longer. In this case, the clinician may implant the lead without using a sheath because the lead will not adhere to the tissue it contacts during the lead insertion and placement process.

Figure 12A:
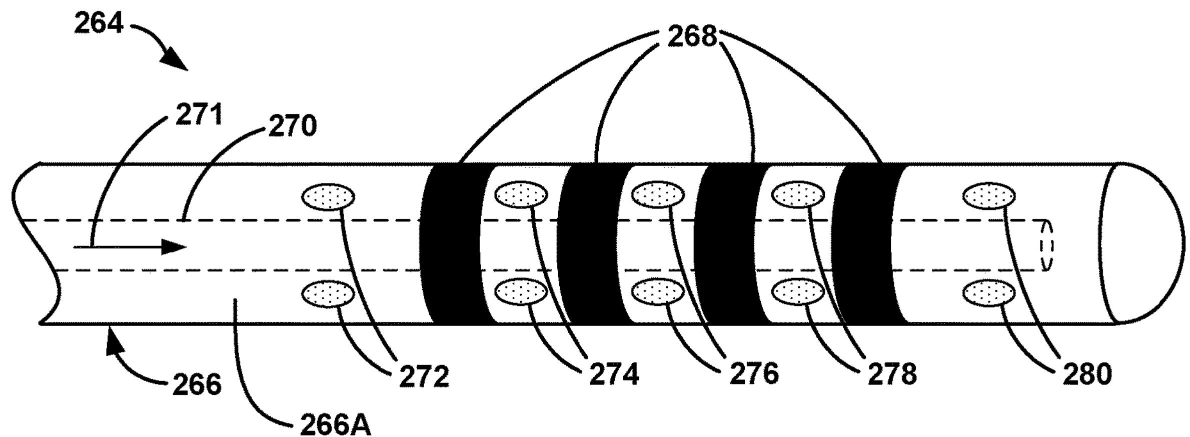
FIGS. 12A and 12B are perspective drawings illustrating exemplary leads with adhesive elements that are activated by energy delivered within the lead.
Figure 12B:
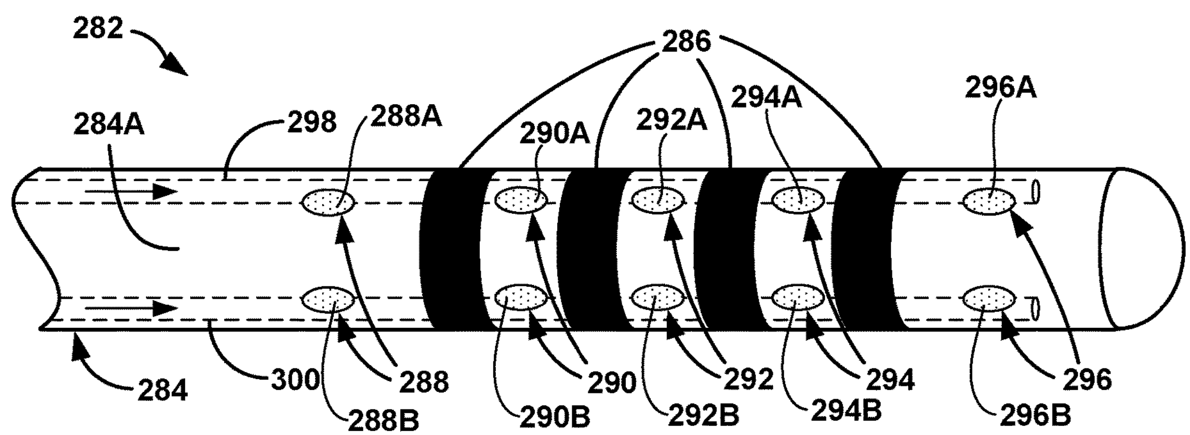

FIGS. 12A and 12B are perspective drawings illustrating exemplary leads 264 and 282 with adhesive elements that are activated by energy delivered within the lead. Leads 264 and 282 may be, for example, embodiments of lead 14 of FIG. 2, lead 204 of FIG. 10A, lead 216 of FIG. 10B or lead 234 of FIG. 10C. As shown in FIG. 12A, lead 264 includes lead body 266, electrodes 268, and adhesive elements 272, 274, 276, 278 and 280 disposed on longitudinal outer surface 266A of lead body 266. In addition, conduit 270 is disposed within lead body 266 and sealed from patient 16. Adhesive elements 272-280 are inactive until adhesive elements 272-280 are exposed to an energy source that is delivered via conduit 270. The energy may be ultraviolet (UV) light that is transmitted down conduit 270 and deflected out to adhesive elements 272-280. Once activated, adhesive elements 272-280 adhere to the adjacent tissue to substantially fix a position of lead 264 proximate to a target tissue site. In addition, an energy may be used to deactivate adhesive elements 272-280 to removed lead 264 from patient 16.

In order to deliver the UV light (or other energy source) to the distal end of lead body 266 to cure adhesive elements 272-280, a clinician may direct UV light from a UV light source from a proximal end of conduit 270, which is typically near the proximal end of lead 264, to a distal end of conduit 270 (in the direction indicated by arrow 271). Conduit 270 may be a fiber optic bundle that includes branches for directing the UV light each adhesive element 272-280 disposed on the outer surface of lead body 266.

In other embodiments, conduit 270 may be a semi-reflective tube to which UV light is delivered. The semi-reflective tube may be configured to reflect UV light out toward adhesive elements 272-280 as the UV light passes through conduit 270. In this case, lead body 266 may be transparent to UV light in at least portions of lead body 266 near adhesive elements 272-280. In alternative embodiments, conduit 270 may be a fiber optic bundle that terminates at a light diffracting device at the distal tip of lead body 266. The light diffracting device may direct the UV light to adhesive elements 272-280 through the transparent (or partially transparent) lead body 266 to cure the adhesive elements 272-280. In all embodiments, lead 264 is at least partially flexible to allow the clinician to implant lead 264 at the appropriate site within patient 16.

With all embodiments, it may be beneficial to limit the exposure of patient 16 tissue to the UV light. Therefore, lead 264 may be constructed to direct the UV light to adhesive elements 272-280 and prevent excess light from contacting the surrounding tissue. UV light is described herein, but other energies may be used in alternative embodiments. For example, infrared light, radio frequency (RF) coupled thermal energy, conductive heating, or other energies may be used to cure adhesive elements 272-280.

Adhesive elements 272-280 may be constructed of a material that is curable by an energy source delivered through lead 264. The adhesive material may be a polymer or resin such as N-vinyl pyrrolidone, polyester polyol acrylates, or other types of curable and biocompatible materials. Each adhesive element 272-280 may be a liquid, gel, or solid prior to being cured. Once cured by the UV light, the adhesive elements may change phase to a solid or very "sticky" gel that engages with the surrounding tissue. In FIG. 12A, adhesive elements 272-280 are shown as round shapes. In other embodiments, however, adhesive elements 272-280 may be constructed in any shape or size to secure lead 264 to the adjacent tissue.

In some embodiments, a sheath may cover adhesive elements 272-280 until the energy source is directed at adhesive elements 272-280 and the curing process begins. The sheath may help the adhesive elements 272-280 from prematurely adhering to surrounding tissue and/or may help protect the adhesive elements 272-280 from damage as lead 264 is implanted in patient 16. In embodiments in which adhesive elements 272-280 are substantially solid prior to being cured, a sheath may not be needed to prevent adhesive elements 272-280 from being prematurely activated or damaged.

FIG. 12B shows lead 282, which is an embodiment of lead 264 of FIG. 12A. Lead 282 includes lead body 284, electrodes 286, adhesive elements 288, 290, 292, 294 and 296, and conduits 298 and 300. Similar to lead 264, a UV light may be delivered or transmitted to cure adhesive elements 288-996 via conduits 298 and 300. Lead body 284 and the conduits 298 and 300 have different central axes. Instead, conduits 298 and 300 are located near longitudinal outer surface 284A of lead body 284 to minimize the distance between each conduit 298 and 300 and the corresponding adhesive elements. In addition, this arrangement helps separate conduits 298 and 300 may help a clinician selectively activate adhesive elements 288-296. For example, if the clinician desires to activate adhesive elements 288A-296A on one side of lead body 284A, the clinician may only direct a UV light down conduit 298. Because conduits 298 and 300 are substantially separated, the UV light may not cure the adhesive elements 288B-296B.

Conduits 298 and 300 may be any type of light transmitting device described above with respect to conduit 270 of FIG. 12A. In some embodiments, lead 282 may employ more than two conduits. For example, one conduit may be used to cure all adhesive elements that share a circumferential location with respect to lead 282. Alternatively, each adhesive element 288-296 may include a dedicated conduit, such as a fiber optic, that runs from the UV light source at the proximal end of lead 282 to the location of the respective adhesive element. In this manner, no branching conduits or diffracted UV light is needed to cure the adhesive elements and secure lead 282 within patient 16.

Figure 13:
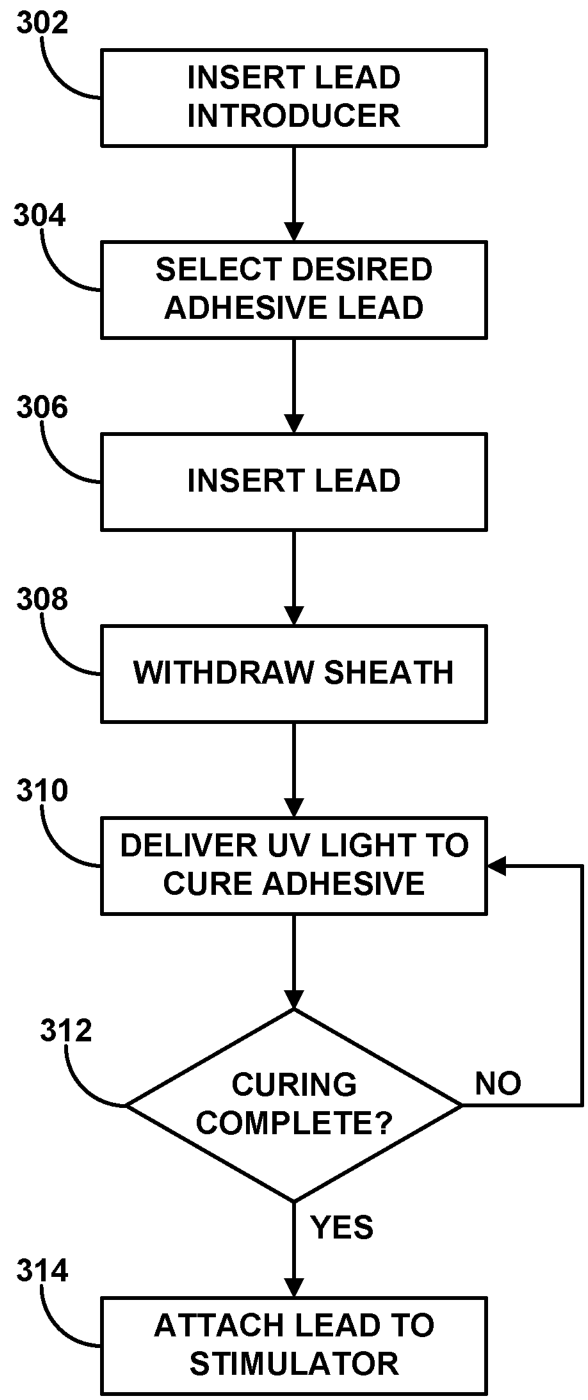
FIG. 13 is a flow diagram illustrating an exemplary process for securing a lead to a tissue of a patient using a UV light curable adhesive element.

FIG. 13 is a flow diagram illustrating an exemplary process for securing a lead to a tissue of a patient using a UV light curable adhesive element. While lead 264 is referenced throughout the description of FIG. 13, in other embodiments, the process shown in FIG. 13 may also be used to implant any of leads 14, 264 or 282. First, the clinician inserts a lead introducer into patient 16 proximate to the target tissue site (302). The tissue site may be adjacent to the sacral nerve, occipital nerve, any other nerve or other tissue site which may provide effective therapy to patient 16 or any suitable therapy deliver site in a patient. Next, the clinician selects the appropriate lead with adhesive elements positioned to best secure the lead without damaging tissue (304). For example, the clinician may select between leads including different adhesive element arrangement about the respective lead body. The clinician then inserts lead 264 into the lead introducer until electrodes 268 of lead 264 are placed correctly (306).

The clinician next withdraws the lead introducer and sheath (if a sheath is used) that separates lead 264 from the surrounding tissue (308). Once the sheath has been removed, the clinician delivers UV light into lead 264 via conduit 270 to cure the adhesive elements 272-280 and adhere lead 264 to the surrounding tissue (310). If the curing is not complete (312), the clinician continues to deliver the UV light to secure lead 264 (310). If the curing is complete and lead 264 is secured to the surrounding tissue (312), the clinician may attach the proximal end of lead 264 to neurostimulator 12 (314) and continue with steps necessary to deliver simulation therapy to patient. As previously discussed, in some embodiments, the adhesive elements 272-280 may be constructed such that a sheath is not needed for the implantation process because the adhesive elements do not interact with the tissue until the UV light is delivered and/or because the adhesive elements are configured withstand the implantation procedure (e.g., introduction of lead 264 into the introducer (306) will not displace the adhesive elements).

As previously discussed, a lead in accordance with the invention may be substantially fixed proximate to a target tissue site with one or more in situ formed fixation elements. In the embodiments described above, the in situ formed fixation element is in the form of an adhesive (whether it is an element disposed on a longitudinal outer surface of a lead body or a solidifying material that flows through a conduit in the lead body) that bonds the lead to adjacent tissue. In another embodiment, the in situ formed fixation element is a fixation structure extending from a lead body, where the fixation structure engages with surrounding tissue to substantially fix a position of the lead.

Figure 14A:
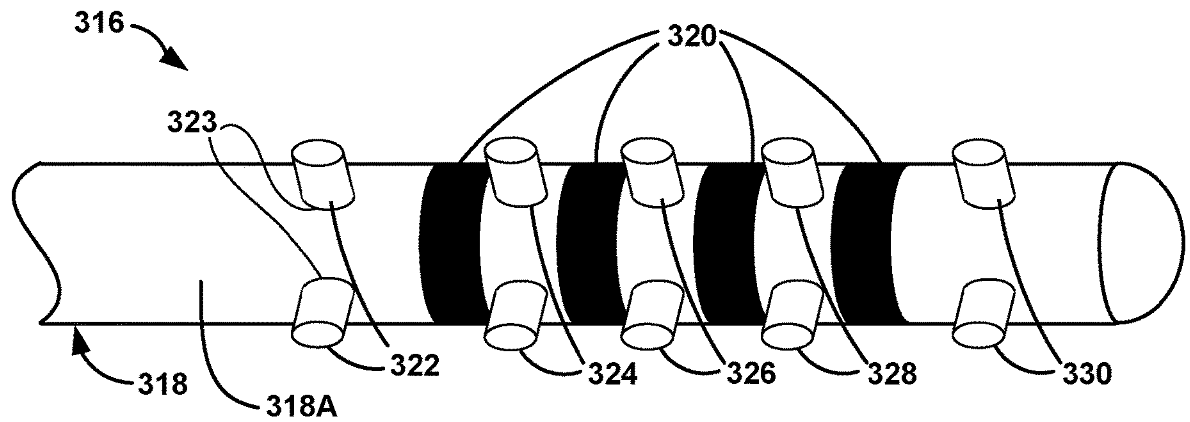
FIGS. 14A and 14B are perspective drawings illustrating exemplary leads with fixation structures extending from the lead body.
Figure 14B:
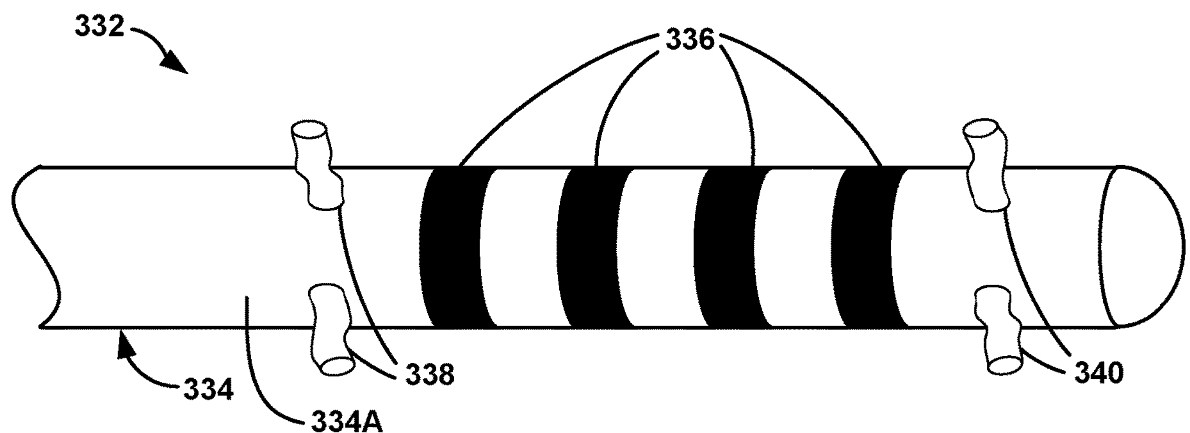

FIGS. 14A and 14B are perspective drawings illustrating exemplary leads with in situ formed fixation structures extending from the lead body. Leads 316 and 322 are embodiments of lead 14. As shown in FIG. 14A, lead 316 includes lead body 318, electrodes 320, and fixation structures 322, 324, 326, 328 and 330. Lead 316 may also include fixation structures on the opposite side of lead body 318 from fixation structures 322-330. Each fixation structure 322-330 extends in a general radially outward direction away from lead body 318 and engages with adjacent tissue of patient 16 to secure the location of lead 316. In some embodiments, fixation structures 322-330 extend from lead body 318 in both an axial and radial direction (e.g., fixation structures 322-330 extend from lead body 318 at an acute angle with respect to longitudinal outer surface 318A of lead body 318), which may help lead 316 resist movement in both radial and axial directions.

Fixation structures 322 are provided at the proximal side of electrodes 320 while fixation structures 330 are located on the distal side of the electrodes 320. Fixation structures 324, 326 and 328 are located between electrodes 320 to prevent the electrodes 320 from migrating. In some embodiments, lead 316 may include a fewer or greater number fixation structures, and the optimal number of fixation structures may depend on the intended use of lead 316. For example, only fixation structures 322 may be used when it is preferable that tissue surrounding the distal tip of lead 316 is not disturbed or fixation structures on only one circumferential area of the lead may be used if a nerve runs along the opposing circumferential area of the lead. An example of such an arrangement of fixation structures is described in commonly assigned U.S. Pat. No. 8,688,238 by Martin T. Gerber, entitled, "IMPLANTABLE MEDICAL ELONGATED MEMBER INCLUDING FIXATION ELEMENTS ALONG AN INTERIOR SURFACE" and filed on the same date as the present disclosure, the entire content of which is incorporated herein by reference. In addition, lead 316 may also include a sheath that covers lead body 318 until fixation structures 322-330 are formed.

Fixation structures 322-330 are formed by a solidifying substance that flows out from exit ports defined by longitudinal outer surface 318A of lead body 318, where the exit ports are in fluidic communication with conduits (not shown) residing within lead body 318. For example, fixation structures 322 flow out of respective exit ports 323. The conduits and exit ports may be any suitable conduits and exit ports, such as the ones described with respect to FIGS. 6A-6D and 7A-7D (e.g., conduits 114 and 118 and exit ports 116, 120 or 122 of FIGS. 6A-6D). Once lead 316 is correctly positioned such that electrodes 320 are located proximate to the target tissue, the clinician may introduce the solidifying substance into the conduits (at the proximal end of lead 316). Upon introduction of the solidifying substance into the conduits, the solidifying substance flows toward the distal end of lead 316 (shown in FIG. 14A). Once the solidifying substance exits the exit ports, the substance hardens and is pushed out from lead body 318 as more substance exits each exit port and hardens. The process continues to form a solid fixation structure that extends from lead body 318 into the surround tissue to secure electrodes 320 in correct position. The length of the fixation structure extending from lead body 318 may be between 1 mm and 10 mm. However, other lengths may also be produced. The resulting size of each fixation structure 322-330 may be controlled by, for example, controlling the amount of solidifying substance that is introduced into the conduits. A certain volume of solidifying substance may be generally equal to a particular range of sizes of fixation structure 322-330.

The solidifying substance may be a polymer, resin, fluid, gel, or other substance that hardens when it comes into contact with moisture or heat, or cools as it travels down lead 316. The solidifying substance is preferably biocompatible, and may be bioresorbable in certain implementations. For example, the solidifying substance may be degraded by normal physiological pathways over a period of days, weeks, months, or even years. Possible materials may include 2-octyl cyanoacrylate, fibrin glue, epoxy, silicone, or a polymer with a melting point higher than 37 degrees Celsius, e.g., a derivative of polypropylene or polyethylene.

In general, the shape of the exit ports dictates the shape of fixation structures 322-330. Thus, in other embodiments, the shape of fixation structures 322-330 may be changed from cylindrical to another shape by modifying the shape of the exit port that the solidifying substance passes through. For example, the exit port may be square to create a cubical shape or rectangular to increase the shear strength of each fixation structure in the direction the shear stress is predicted to occur, e.g., in the axial direction of lead 316. In other embodiments, the exit ports may be angled to extend the fixation structures at an acute angle with respect to longitudinal outer surface 318A of lead body 318.

FIG. 14B shows lead 332, which is an embodiment of lead 316. Lead 332 includes lead body 334, electrodes 336, and fixation structures 338 and 340. Fixation structures 338 are located proximal to electrodes 336 and fixation structures 340 are located distal to electrodes 336. Fixation structures 338 and 340 are formed from smaller exit ports than fixation structures 322-330 of lead 316. The smaller exit ports may result in fixation structures 338 and 340 that extend further from longitudinal outer surface 334A of lead body 334, which may allow fixation structures 338 and 340 to penetrate deeper into surrounding tissue. As shown, fixation structures 338 and 340 are not cylindrical in shape. As the solidifying substance is forced out of the exit ports, the created fixation structure may move to one or more directions that offer the least resistance to the structure. In this manner, the resulting fixation structures 338 and 340 are irregularly shaped. However, even irregularly shaped fixation structures 338 and 340 may engage with surrounding tissue to secure lead 332. In general, each fixation structure 338 and 340 may have a diameter between 0.5 millimeter (mm) and 5 mm. In addition, the height of each fixation structure 338 and 340 may be generally between 0.5 mm and 10 mm away from lead body 334. However, dimensions smaller or larger than those listed may also be used by lead 332.

Therapy may require that a stimulation lead be activated for only a short period of time, e.g., for trial stimulation, sometimes referred to as screening. On the other hand, therapy may require that the stimulation lead be implanted chronically for a number of years. In either case, it may become necessary to remove (or "explant") the stimulation lead from patient 16.

In one embodiment, leads 316 and 332 may include in situ formed fixation elements that are dissolvable in order to aid removal of leads 316 or 332 from patient 16 without damaging the surrounding tissue. For some solidifying substances, the clinician may flow a degrading fluid (or a dissolving agent) down the conduits within the lead body to liquefy the solidifying material, and in particular, to weaken or break off the point at which the fixation structure attaches to the lead body so that the fixation structure breaks from the lead body. In other embodiments, the clinician may heat the lead until the fixation device softens so that the lead can be removed without the fixation structure damaging surrounding tissue as the lead is withdrawn from patient 16. Alternatively, the clinician may force a sheath onto the lead and sever the fixation structures from the lead body.

In other embodiments, leads 316 and 332 may be removed from patient 16 by overcoming the secure strength of the fixation elements. The fixation elements may be formed to have a strength sufficient for preventing migration of the lead during normal patient 16 activity and movement. However, the fixation structures may be fractured and broken off from leads 316 or 332 when the clinician attempts to pull either lead out from patient 16. The failure point may be low enough that the force from removal does not cause severe tissue damage. Alternatively, the fixation elements may yield or bend from the removal force of the clinician to free leads 316 and 332 without causing extensive tissue damage. This method of breaking the fixation structures for lead removal may also be applied to the solidifying substance when it is used as an adhesive or adhesive element as well. In other words, the adhesive bond to the adjacent tissue may be broken without causing severe tissue tearing or damage.

FIGS. 14A and 14B illustrate the exterior surface of leads 316 and 332, and the conduits that deliver the solidifying substance is not shown. Both leads 316 and 332 may utilize a conduit system as described for leads 108 and 140 of FIGS. 6A-D and 7A-D, respectively. Both conduit systems are designed to flow a solidifying substance from the proximal end of the lead to the distal end of the lead, but the components of the solidifying substance or the flow rate or temperature of the substance may be varied in leads 316 and 322 to create the fixation structures in situ.

Figure 15:
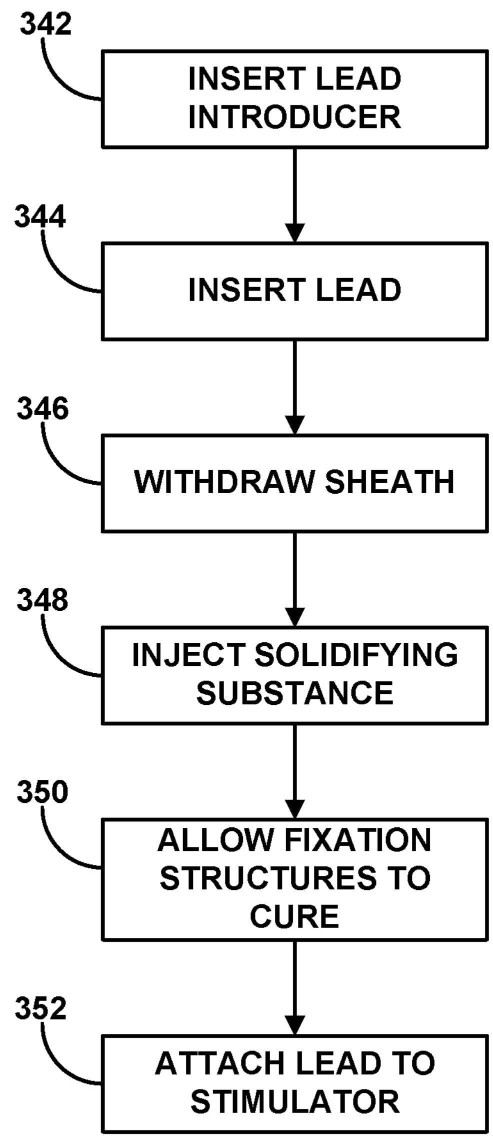
FIG. 15 is a flow diagram illustrating an exemplary process for securing a lead to a tissue of a patient using fixation structures formed in situ.

FIG. 15 is a flow diagram illustrating an exemplary process for securing a lead to a tissue of a patient using fixation structures formed in situ. While lead 316 is referenced throughout the description of FIG. 15, a clinician may also implant any lead including in situ formed fixation structures (e.g., leads 14 or 332) in accordance with the process shown in FIG. 15. First, the clinician inserts a lead introducer into patient 16 proximate to the target tissue site (342). The tissue site may be adjacent to the sacral nerve, occipital nerve, any other nerve which may provide effective therapy to patient 16 or any other suitable target therapy deliver site. Next, the clinician inserts lead 316 into the lead introducer until electrodes 320 of lead 316 are placed proximate to the target tissue site (344). The clinician next withdraws the lead introducer and sheath (if used) that covers lead 316 from the surrounding tissue (346).

After the clinician has removed the introducer and sheath, the clinician attaches or otherwise couples a supply of solidifying substance to a conduit within lead body 318. The solidifying substance is injected (or otherwise moved through) into the conduits of lead 316 until the substance extends from lead body 318 to form the fixation structures 322-330 that engage with surrounding tissue to substantially fix at least the distal end of lead 316 within patient 16 (348). The solidifying substance may be provided by a fluid pump, a syringe, a plunger, a gravity feed bag, or any other device that could be coupled to lead 316. The device may be automatically controlled by a processor or manually controlled by the clinician. The clinician waits a predetermined amount of time to allow the fixation structures to cure or until the clinician can determine independently that the fixation structures are solid, e.g., by slightly pulling on lead 316 to check for movement (350). Once the lead is secure, the clinician can tunnel a proximal end of lead 316 to the location of the implanted neurostimulator 12 and mechanically and electrically couple the lead to the neurostimulator (352).

Figure 16:
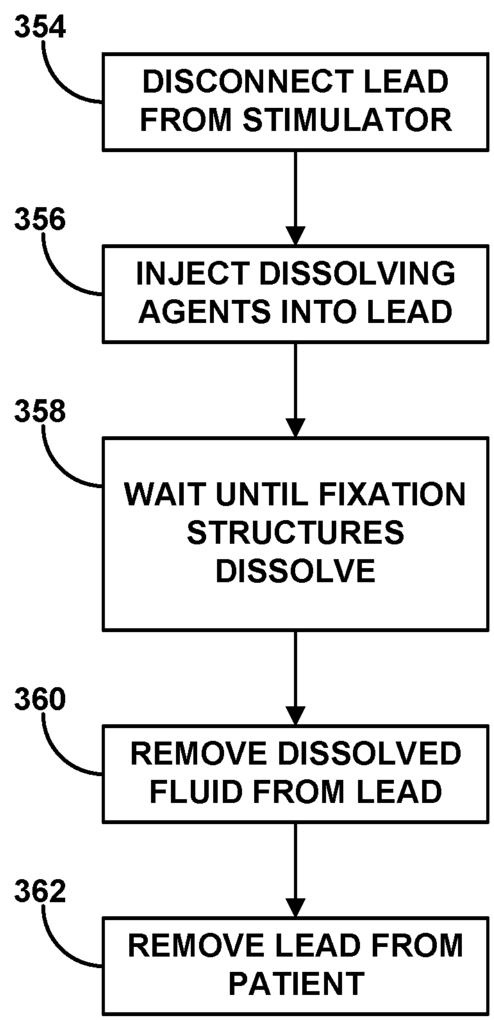
FIG. 16 is a flow diagram illustrating an exemplary process for removing a lead from a tissue of a patient by dissolving the solidified structures.

FIG. 16 is a flow diagram illustrating an exemplary process for removing a lead from a tissue of a patient by dissolving fixation structures, such as fixation structures that were formed in situ using the process shown in FIG. 15. Any of leads 14, 60, 68, 76, 92, 100, 108, 140, 316 or 332 may be removed in this manner, but lead 316 will be used as an example. The clinician begins by prepping patient 16 for removal of the lead by disconnecting lead 316 from neurostimulator 12 (354). The clinician next uses a syringe to inject a dissolving agent into the conduits that are coupled to the exit ports used to form to fixation structures 322-330 (356). The syringe may be pre-loaded with the correct volume of dissolving agent needed to liquefy the fixation structures. Alternatively, devices other than a syringe may be used to deliver the dissolving agent. The clinician waits for the dissolving agent to dissolve or liquefy the fixation structures 322-330 (358). Once liquefied, the clinician may remove the dissolved solidifying substance from lead 316 (360). Alternatively, the dissolved substance may be deposited into the adjacent tissue where it is removed by the clinician or degraded in vivo. In some embodiments, the clinician may need to repeat steps 356-360 until the fixation structures are free of lead body 318. Once all fixation structures no longer secure lead 316 within the tissues of patient 16, the clinician may remove the lead from the patient (362).

In some embodiments, any remaining fixation structures in patient 16 may be arthroscopically removed by the clinician or degraded in vivo over time by normal degradation processes. In other embodiments, the fixation structures may be benign and remain within patient 16. Alternative to using a dissolving substance, the clinician may use a sheath to shear the fixation structures from lead body 318 or heat or a solvent to soften fixation structures 322-330 so that lead 316 can be removed from patient 16 without rigid fixation structures 322-330, which may help limit damage to surrounding tissue as lead 316 and fixation structures 322-330 are withdrawn from patient 16.

Figure 17A:
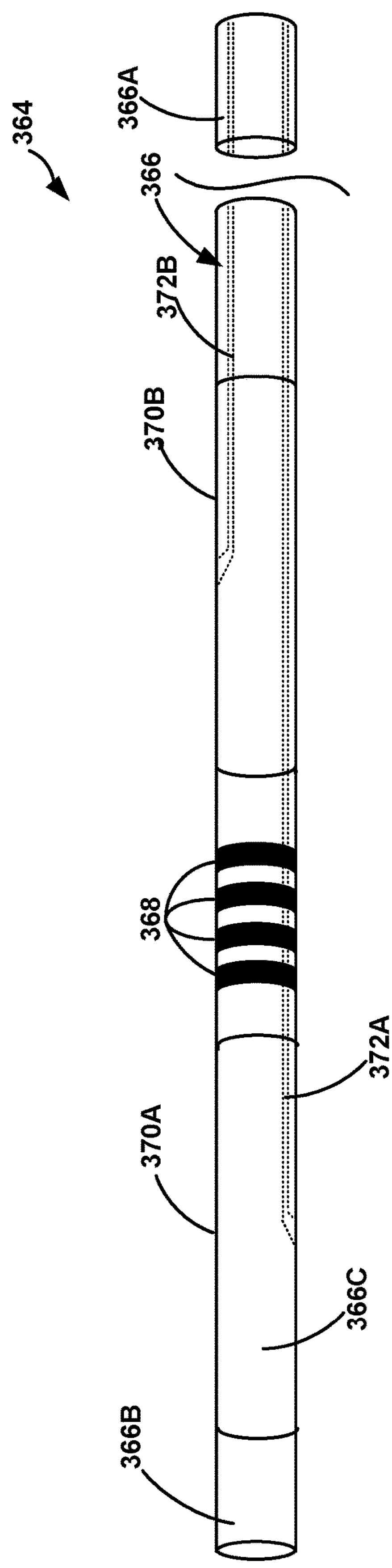
FIGS. 17A and 17B are perspective drawings illustrating an exemplary stimulation lead that may be fixated to surrounding tissue to reduce migration of the lead following implantation.
Figure 17B:
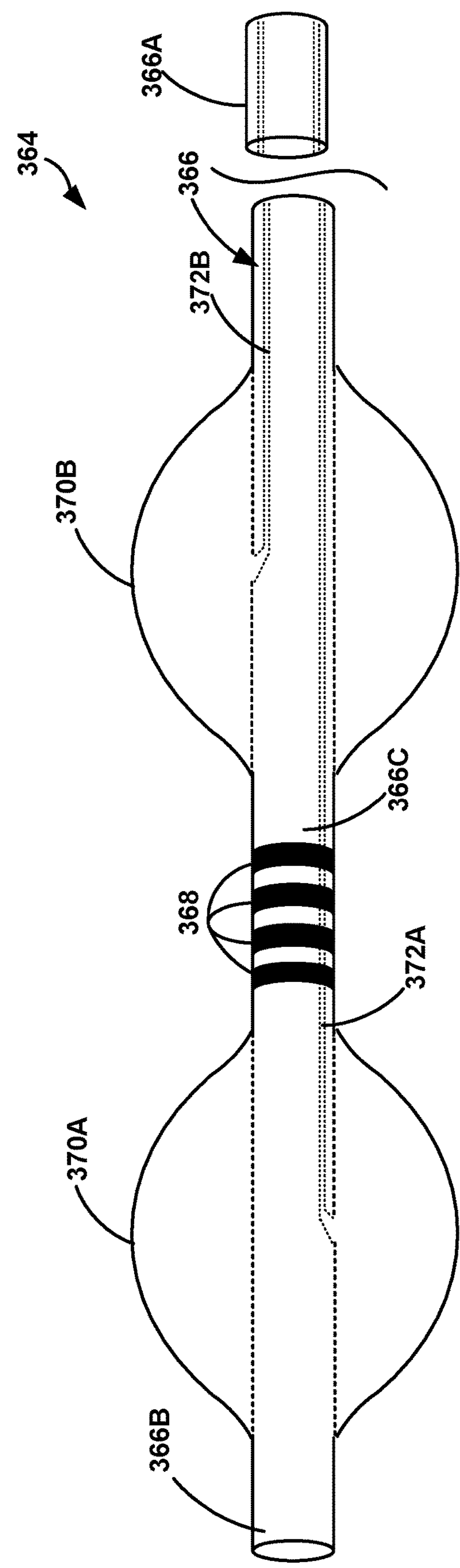

FIGS. 17A and 17B are perspective drawings illustrating an exemplary stimulation lead that may be fixated to surrounding tissue to discourage migration of the lead following implantation. As shown in FIG. 17A, stimulation lead 364 includes a lead body 366 extending between proximal end 366A and proximal end 366B, a plurality of stimulation electrodes 368, and a fixation device consisting of balloon elements 370A and 370B (collectively "balloon elements 370"). Located within lead body 62 are inflation lumens 372A and 372B (collectively "inflation lumens 372"), which are shown in phantom lines. Inflation lumen 372A is in fluidic communication with balloon 370A, while inflation lumen 372B is in fluidic communication with balloon 370B.

As described above, stimulation lead 364 carries a number of stimulation electrodes 368 to permit delivery of electrical stimulation to a target stimulation site such as a sacral nerve (FIG. 1A) or an occipital nerve (FIG. 1B). Lead body 366 of stimulation lead 364 includes one or more conductors to electrically couple electrodes 368 to terminals within neurostimulator 12. In particular, proximal end 366A of lead body 366 includes electrical contacts (not shown in FIGS. 17A and 17B) that electrically connect electrodes 368 (via the conductors) to a lead extension or a neurostimulator (e.g., neurostimulator 12 in FIG. 1A).

In practice, balloon elements 370 facilitate fixation of stimulation lead 367 to surrounding tissue, e.g., within or posterior to sacral foramen 22 (FIG. 1A). Balloons 370 are configured to expand radially outward from lead body 366 in order to engage with surrounding tissue to help prevent migration of lead 366 from the target stimulation site. While "radially outward" is referred to throughout the disclosure, it should be understood that the expansion of balloons 370 may include both axial and radial components because balloons 370 may extend from lead body 366 at an acute angle with respect to outer surface 366C of lead body 366.

Balloon elements 370 are inflated by a solidifying substance delivered to the balloon elements via conduits 372A and 372B (collectively conduits 372). Each balloon element 370A and 370B may be sized to be expandable to a diameter sufficient to fixate lead 364 within a target site. For example, balloon elements 370 may be expandable to a diameter in a range of approximately 2 millimeters (mm) to 10 mm, and in one embodiment, approximately 4 mm to 6 mm, when disposed within a tissue site proximate the sacral foramen 22 in the presence of compressive forces generated by typical tissue. In another embodiment, balloon elements 370 may facilitate fixation of stimulation lead 364 to tissue surrounding the lead in other target sites. If lead 364 is implanted in the epidural region around the spine, for example, balloon elements 364 may be expandable to a diameter in a range of approximately 6 mm to 15 mm, and in one embodiment, approximately 9 mm to 12 mm. In each scenario, a predetermined amount of fluid may be added to balloons 66 to expand balloons 66 to the desired dimension.

While balloon elements 370 may be formed to be of equal size and shape, in some embodiments, it may be desirable for the balloon elements 370 to differ in size and/or shape with respect to each other to best secure lead 364 within patient 16. For example, the size and/or shape of each of balloon elements 370 may be modified to accommodate the specific anatomical configuration of a region of patient 16 proximate to the target tissue site.

Prior to implantation of lead 364 in patient 16, balloons 370 are each in a first, substantially deflated state as shown in FIG. 17A and have a first dimension. Balloon elements 370 are shown in the unexpanded state in FIG. 17A. Balloon elements 370 may be introduced in an unexpanded state during implantation to permit lead 364 to retain a small overall lead diameter which reduces tissue damage during implantation. In this manner, lead 364 may be deployed via a needle or other minimally invasive delivery device. Introducing lead 364 via a needle requires only minimally invasive techniques which provides reduced tissue damage, reduced patient recovery time, and increased patient comfort.

In a deflated state, balloon elements 370 may be substantially flush with lead body 366. For example, balloons 370 may be disposed within recesses within lead body 366 or otherwise coupled to the outer surface 366C of lead body 366. In alternative embodiments, portions of balloons 370 may slightly protrude from outer surface 366C of lead body 366 in their deflated states. In both cases, a restraint (e.g., sheath 58 of FIG. 3A) may be used to protect, and if necessary restrain, balloons 66 in their deflated state. In some embodiments, the lead introducer may function as restraint 68.

In one embodiment, at least a portion of stimulation lead 364, such as lead body 366, may include radio-opaque material that is detectable by imaging techniques, such as fluoroscopic imaging or x-ray imaging. This feature may be helpful for maneuvering stimulation lead 364 relative to a target site within the body. For example, the distal end 366B of stimulation lead 364 may include radio-opaque material that is visible via fluoroscopic imaging. Radio-opaque markers, as well as other types of markers, such as other types of radiographic markers, may also be employed to assist a clinician during the introduction and withdrawal of stimulation lead 364 from patient 16.

Upon implantation in patient 16, a solidifying substance may be introduced into balloons 370 via inflation lumens 372 such that balloons 370 each expand to a second, expanded state and extend past outer surface 366C of lead body 366 to engage with surrounding tissue. FIG. 17B is a perspective drawing illustrating an exemplary stimulation lead 60 with balloon elements 370 in an expanded state.

In the expanded, inflated state, balloons 370 each have a second dimension, which is greater than the first dimension in the unexpanded, deflated state, thereby enlarging the profile of at least a portion of lead 364. Balloons 370 may be expandable to any suitable diameter, which may depend on the particular stimulation application of lead 364. The solidifying substance inflates balloon elements 370 away from lead body 366 to engage with surrounding tissue, thereby fixing stimulation lead 364 proximate to a target stimulation site. While balloons 370 do not necessarily restrict all motion of lead 364 when balloons 370 are in the inflated state, balloons 370 generally reduce the motion of lead 364 so that lead 364 remains proximate to the target tissue site.

The solidifying substance solidifies within balloon elements 370 to prevent the balloon elements from deflating. The solidifying substance may be solidified, or cured, through one or more techniques. In one embodiment, the solidifying substance solidifies after the heat from surrounding tissue activates the solidifying substance. In another embodiment, the solidifying substance is delivered into balloon elements 370 at a temperature greater than 37 degrees Celsius (normal body temperature). As the solidifying substance cools, the substance hardens and cures within balloon elements 370. In an alternative embodiment, each conduit 372A and 372B may include two separate conduits that deliver two types of fluid to balloon elements 370. Both fluids are inactive when isolated, but the two fluids solidify when combined within the balloon elements 370. In some cases a washer fluid may be introduced between the two different liquid deliveries into balloon elements 370 in order to use only one conduit for both fluids.

In an alternative embodiment, thermal, UV, infrared, or visible radiation may be transmitted down conduits 372 or another conduit in order to cure the solidifying substance. Instead of radiation, body temperature, body chemistry, chemical agents injected into the conduit, or electrical current sent down the conduit may be used to cure the solidifying substance used to inflate balloon elements 370. If balloon elements 370 are located close to the surface of the skin of patient 16, solidifying energy may be applied to the balloon elements through the skin if the energy is benign to the intervening tissue. For example, external heat may be used to increate the temperature of the solidifying temperature to a temperature that will not harm patient 16.

Therapy may require that the stimulation lead be activated for only a short period of time, e.g., for trial stimulation, sometimes referred to as screening. On the other hand, therapy may require that the stimulation lead be implanted chronically for a number of years. In either case, it may become necessary to remove the stimulation lead from the patient. A solvent may be used to return the solidified material to a fluid with a liquid or gel consistency, and then the fluid may be removed from balloon elements 370 via the respective lumen 372 (e.g., via suction). Alternatively, other chemical agents, electrical current, or thermal, UV, infrared, or visible radiation may be used to convert the solidified material from a solid to fluid form and removed through conduits 372 until lead 364 is no longer secured within patient 16.

Figure 18A:
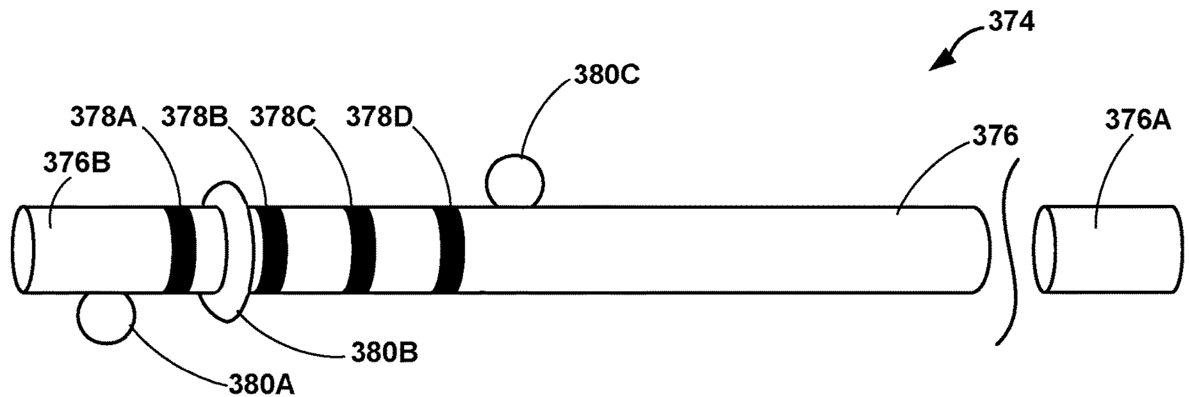
FIGS. 18A-18C are perspective drawings illustrating alternate configurations of the inflatable balloon fixation device mounted on the body of a lead for fixing positions of leads in accordance with the invention.
Figure 18B:
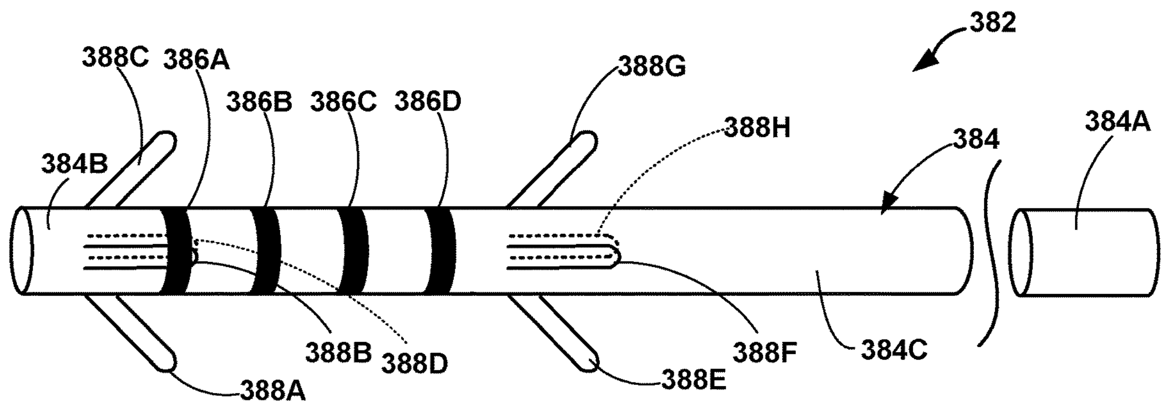
Figure 18C:
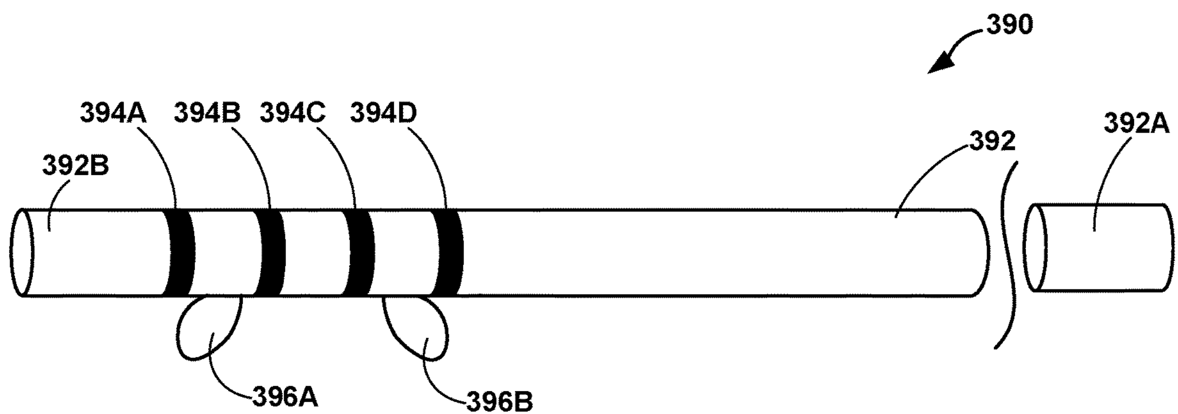

FIGS. 18A-18C are perspective drawings illustrating alternate configurations of the inflatable balloon fixation device mounted on the body of a lead for fixing positions of leads in accordance with the invention. The leads illustrated in FIGS. 18A-18C are shown in their inflated state but are capable of being deflated and inflated using one or more inflation conduits (not shown in FIGS. 18A-18C), as previously described. FIG. 18A illustrates an embodiment of lead 374, which includes lead body 376 extending between proximal end 376A and distal end 376B, electrodes 378A-378D (collectively "electrodes 378") disposed proximate to distal end 376B of lead body 376, and balloon fixation elements 380A-C (collectively "balloons 380"). Balloons 380 provide a predetermined form to guide the solidifying substance into that shape. An inflation lumen (e.g., inflation lumen 372A in FIGS. 17A-17B) may be fluidically connected to each of balloons 380 in order to provide a channel to deliver a solidifying substance to balloons 380 to inflate balloons 380. Each balloon 380 may have its own inflation lumen or two or more balloons 380 may share an inflation lumen.

Balloons 380A-380C (collectively "balloons 380"), which fix lead body 376 at either one or both of the proximal and distal side of electrodes 378 and between two electrodes 378A and 378B. In particular, balloon 380A is located between distal end 376B of lead body 376 and electrodes 378 (i.e., on the "distal side" of electrodes 378), balloon 380B is located between electrodes 378A and 378B, and balloon 380C is located between the proximal end 376A of lead body 376 and electrodes 378 (i.e., on the "proximate side" of electrodes 378). Fixing lead 374 between two electrodes 378A and 378B may provide a more secure position for the electrodes with respect to the surrounding tissue in cases subject to extreme lead deflection or tissue movement.

Balloon 380B in FIG. 18A is shown as extending around the periphery of lead body 376A. The balloons may be distributed around a portion of the periphery of lead body 376 rather than extending substantially around the entire periphery. For example, in contrast to balloon 380B, balloons 380A and 380C extend from a portion of the periphery of lead body 376 rather than extending substantially around the periphery.

In one embodiment, balloons 380A and 380C may extend from only one side of lead body 376 rather than being distributed about the periphery of the lead body. FIG. 18A further illustrates an embodiment of lead 374 in which balloons 380A and 380C located at different axial positions with respect to lead body 376 extend from different sides of the lead body. More specifically, FIG. 18A illustrates balloon element 380A located at a first axial position extending in a first circumferential (i.e., radial) direction, and second balloon element 380C located at a second axial position extending in a second circumferential direction that differs from the first direction. Balloon elements 380A and 380C extend in approximately opposite directions. However, in other embodiments, balloon elements 380A and 380C may each extend in circumferential directions separated by less than 180 degrees.

While fixing lead 374 at either the proximal side or distal side of electrodes 378 may be useful in some applications, in other applications, it may be desirable to fix lead 374 at both the proximal and distal sides of electrodes 378, as depicted in FIG. 18A. Balloon fixation elements located both distally and proximally to electrodes 378 may provide a more secure attachment than simply fixating lead 374 at one portion of the lead body 376. For example, fixing lead 374 on both the proximal and distal sides of electrodes 378 may increase the rigidity of the portion of lead body 376 containing the electrodes 378. This may be useful, for example, in an application in which lead 374 is a part of a therapy system delivering electrical stimulation to a pudendal nerve of patient 16.

FIG. 18B illustrates lead 382, which includes lead body 384 extending between proximal end 384A and distal end 384B and electrodes 386A-386D (collectively "electrodes 386") disposed proximate to distal end 384B of lead body 384. Balloons 388A-388H (collectively "balloons 388") are coupled to lead body 384 to substantially fix a position of lead 382 proximate to a target tissue site. When inflated state with a solidifying material (as shown in FIG. 4B), each of balloons 388 defines a rigid tine-like structure that protrudes from outer surface 384C of lead body 384. An inflation lumen (e.g., inflation lumen 372A in FIGS. 17A-17B) may be fluidically connected to each of balloons 388 in order to provide a channel to deliver a solidifying substance to balloons 388 to inflate balloons 388. Each balloon 388 may have its own inflation lumen or two or more balloons 388 may share an inflation lumen.

As shown in FIG. 18B, balloons 388A-388D are located at a first axial position along lead body 384, and balloon 388E-388H are located at a second axial position with along lead body 384. Balloons 388D and 388H are located on the circumferential portion of lead 382 not visible in FIG. 18B. The approximate locations of balloons 388D and 388H are outlined in FIG. 18B with phantom lines. Additionally, balloons 388A-388D may be, but need not be, evenly distributed around the periphery of lead body 384. Balloons 388A-388D are located on a portion of lead body 384 proximal to electrodes 386, and balloons 388E-388H are located on a portion of lead body 384 distal to electrodes 386. More specifically, balloons 388A-388D are disposed between the most distally located electrode 386A and distal end 384B of lead body 82, and balloons 388E-388H are disposed between the most proximally located electrode 386D and proximal end 384A of lead body 384. Alternatively, one or more balloon elements may be disposed in between individual electrodes 386, e.g. between electrodes 386A and 386B.

Balloons 388, shown in FIG. 18B, are angled in their expanded states such that they have both a radial and axial component. In particular, balloons 388A-H each extend from lead body 384 at an acute angle with respect to outer surface 384C of lead body 384. Balloons 388 are angled toward proximal end 384A of lead body 384. Angling balloons 388 toward proximal end 384A of lead body 384 may aid in limiting migration of lead 382 toward the direction in which the balloons are angled, e.g., toward the insertion site and neurostimulator in the direction of proximal end 384A. In other embodiments, lead 382 may include balloons that also extend toward distal end 384B of lead body 384 when inflated, or alternatively, lead 382 may only include balloons that extend toward distal end 384B.

As an additional alternative, lead 382 may be fixed on both sides of one or more electrodes to reduce lead migration of the electrodes from their target position after implantation. FIG. 18C shows lead 390, which includes lead body 392, electrodes 394A-D (collectively "electrodes 394"), balloon 396A located between electrodes 394A and 394B, and balloon 396B located between electrodes 394C and 394D. Balloons 396A and 396B are generally disposed on the same side of lead body 392. This configuration may locally fixate electrodes 394 as well as generally fix lead 390. For example, locally fixating electrodes 394B and 394C may useful in applications where a clinician aims to implant lead 390 such that the mid-length of the electrode region of lead body 392, i.e., the location between electrodes 394B and 394C, is centered at the target stimulation site. Alternatively, balloons 396 may be positioned to locally secure other electrodes 394.

In FIG. 18C, balloon 396A on lead 390 is shown angled toward distal end 392B of lead body 392 and away from electrode 394B. Balloon 396B is shown angled toward proximal end 392A of lead body 392 and away from electrode 394C. If a clinician aims to implant lead 390 such that the mid-length of the electrode region of lead body 392, i.e., the location between electrodes 394B and 394C, is centered at the target stimulation site, it may be desirable to angle balloons 396A and 396B away from the mid-length of the electrode region. This configuration may allow electrodes 394B and 394C to have more direct contact with the target stimulation site. Alternatively, multiple balloons may be positioned at equal or unequal circumferential positions around lead body 392 at one or more axial positions along the longitudinal surface of lead body 392.

In general, one or more balloons may be used in fixating a lead. One or more of these balloons may be filled with a solidifying material. Additionally, other fixation elements may be used in addition to balloons. For example, tines may be added to any of the illustrated embodiments to provide a more addition fixation devices. If additional fixation elements are used in addition to balloons, all of the fixation elements may be restrained during implantation of the lead and expanded upon implantation. This may be done with a sheath, as described above in FIGS. 3A-B. Also, all of the fixation devices may be configured to permit explanation of the lead after therapy is no longer desired.

In some embodiments, the inflatable balloons of FIGS. 17 and 18 may be filled with a solution that is capable of being solidified. As described above, the solidifying substance may be solidified or cured using a second solidifying material, thermal, UV, infrared, or visible radiation, body temperature, body chemistry, chemical agents injected into the inflation conduit, or electrical current sent down the inflation conduit in any embodiments described herein. The solidifying substance inside of the balloons may aid in fixing the lead in a location proximate to a target stimulation tissue site. Once the substance is cured, it may return to a liquid state upon introduction of a solvent. The liquefied substance may be removed from the balloon to remove the lead from patient 16 with minimal tissue damage.

Figure 19:
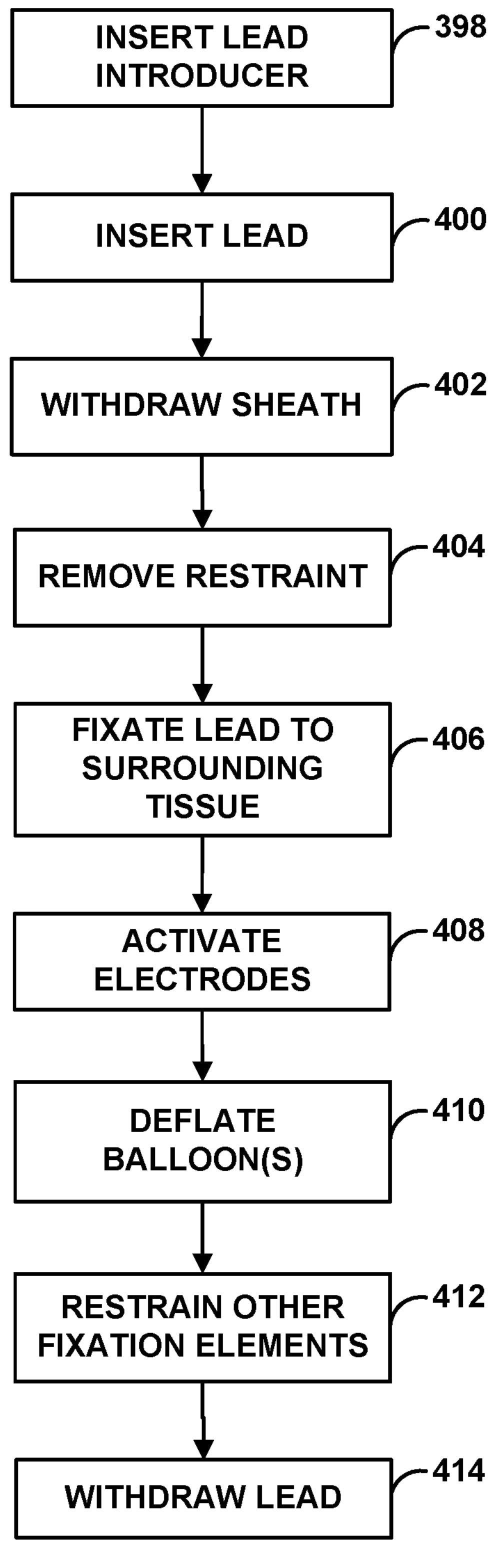
FIG. 19 is a flow diagram illustrating a process for percutaneously implanting a lead including a fixation device in accordance with one embodiment of the invention.

FIG. 19 is a flow diagram illustrating a process for percutaneously implanting a lead including a fixation device in accordance with one embodiment of the invention. While the process shown in FIG. 19 is described with respect to lead 364 of FIGS. 17A and 17B, the process may be used to implant any suitable lead, such as any one of leads 376, 382 or 390 of FIGS. 18A-18C, respectively. Alternatively, the process shown in FIG. 19 may be used to implant any suitable lead including a fixation device with balloon-type elements that are expandable with a solidifying substance as described herein.

Initially, an introducer needle assembly is inserted into a patient (398). The needle assembly may include a needle and an introducer stylet fitted into a lumen defined by the needle. In one embodiment, the lumen has a diameter between 14 and 20 gauge to allow the needle to receive the introducer stylet. The introducer stylet may fill the lumen of the needle, preventing tissue coring. In some instances, the needle may include a straight needle for sacral implantation or a modified Tuohy needle for epidural applications, which has an opening that is angled approximately 45 degrees so that an instrument passing through the needle exits at an angle. The stimulation lead introducer may be inserted by a variety of techniques not limited to the technique described above.

Lead 364 is inserted into the patient and advanced through the lead introducer by the clinician until it reaches the desired therapy stimulation tissue site (400). During the insertion process, balloons 370 are in a deflated state and a restraint mechanism, may protect the balloons damage during insertion. A restraint mechanism, such as the lead introducer, a sheath other than the lead introducer, a stylet, or the like, may also serve to restrain other expandable fixation elements that may optionally be included on the lead. Once the stimulation lead reaches the target stimulation site, the lead introducer is withdrawn (402). In one embodiment, the restraint mechanism includes the lead introducer. In this case, the act of withdrawing the lead introducer exposes balloons 66 and removes the restraint on any additional fixation elements. The restraint mechanism is removed after the lead introducer (404); however, some embodiments may not include an additional restraint.

After the stimulation lead 364 has been properly placed proximate to a target stimulation site, balloons 370 are inflated to allow balloons 370 to extend from lead body 364 and engage with surrounding tissue to fix lead 364 to surrounding tissue (406), e.g., in an epidural region proximate the spine or a sacral foramen. Fixing lead 364 to surrounding tissue may prevent detrimental effects in therapy that may result from a migrated stimulation lead.

Balloons 370 may be inflated by injecting a solidifying substance through inflation conduits 372. The solidifying substance may be in fluid as it is introduced into conduits 372 and flows into the respective balloons 370. In some embodiments, the fluid, or solidifying substance, includes two fluids that cause the substance to cure once the fluids come into contact with each other. Alternatively, thermal, UV, infrared, or visible radiation, body temperature, body chemistry, chemical agents injected into the inflation conduits 372, or electrical current sent down the inflation conduits 372 may be used to solidify the solidifying substance.

Electrodes 368 on lead 364 may be activated (408) to provide therapy to the patient, e.g., by coupling a proximal end 366A of stimulation lead body 366 to a neurostimulator (e.g., neurostimulator 12 of FIGS. 1 and 2). In one embodiment, a lead extension may be provided to couple the stimulation lead to the neurostimulator.

Therapy may require that the stimulation lead 364 be activated for only a short period of time, e.g., for trial stimulation, sometimes referred to as screening. On the other hand, therapy may require that lead 364 be implanted chronically over a period of many years. In either case, it may become necessary to remove lead 364 from patient 16. Balloons 370 may be deflated (410), and if other fixation elements were included on the lead body, they may be restrained as they were when the lead 364 was inserted (412).

Balloons 370 may be deflated by first liquefying the solidifying substance and then removing the liquid from the balloon via inflation conduits 372. A solvent may be delivered via inflation conduits 372 may be used to liquefy the solidifying substance. Alternatively, thermal, UV, infrared, or visible radiation, chemical agents injected into the inflation conduits, or electrical current sent down the inflation conduits may be used to liquefy the material. Once all of the fixation elements are deflated or restrained, the stimulation lead may be withdrawn from the patient (414).

Figure 20A:
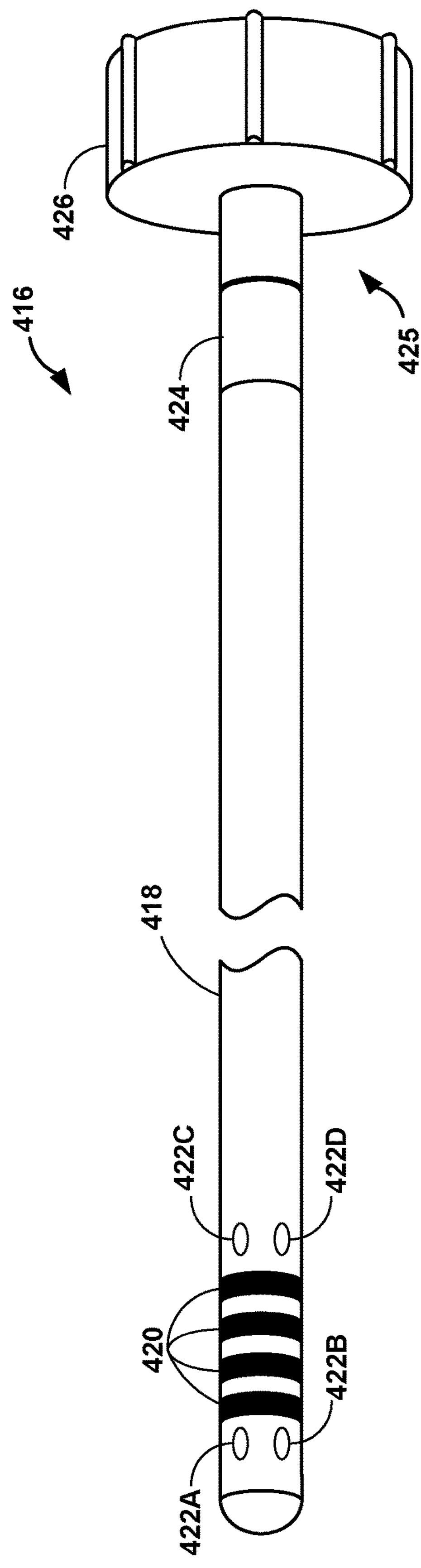
FIGS. 20A and 20B are perspective and cross-sectional drawings illustrating a stylet that is inserted through a conduit that delivers a solidifying substance.
Figure 20B:
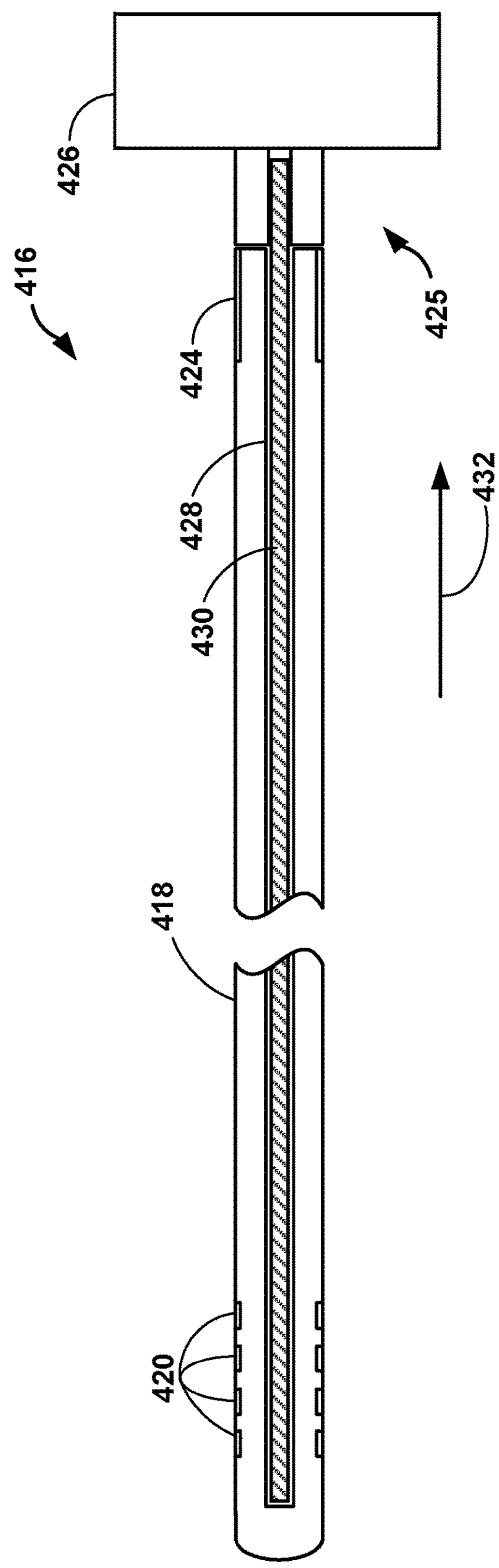

FIGS. 20A and 20B are perspective and cross-sectional drawings illustrating a stylet that is inserted through a conduit that delivers a solidifying substance. As shown in FIG. 20A, lead 416 includes elongated member 418, electrodes 420, exit ports 422A-D (collectively "exit ports 422), and conductor 424. Lead 416 also includes stylet 425 that includes handle 426 and a shaft (not shown) within elongated member 418. The clinician uses stylet 425 to manipulate and bend the distal tip of elongated member 418 to guide lead 416 through patient 16 and reach the target tissue. In some embodiments, a sheath (not shown) may also cover lead 416 prior to reaching the target tissue.

FIG. 20B shows the cross-section of lead 416 and stylet 425. Shaft 430 is attached within handle 426 of stylet 425, and shaft 430 is configured to fit within conduit 428 of elongated member 418. Conduit 428 may be considered a dual purpose conduit, e.g., conduit 428 is configured to accept shaft 430 and deliver a solidifying substance to patient 16 via exit ports 422. Shaft 430 may be constructed of an axially stiff and bendable metal alloy or polymer, similar to other stylet shafts of lead guidance systems commonly known in the art. Handle 426 may be constructed of a metal alloy or polymer that is configured to be manipulated with fingers of the clinician. As mentioned above, shaft 430 is used by the clinician to change the shape of elongated member 418 and facilitate the insertion and placement of lead 416 within patient 16. Once, the clinician has correctly placed lead 416, the clinician may remove stylet 425 from lead 416 in the direction of arrow 432. The clinician may then deliver a solidifying substance through conduit 428, as described herein and in FIG. 21.

Conduit 428 is shown to have a common central axis to elongated member 418. However, some embodiments may be configured with conduit 428 within a side of elongated member 418, such that conduit 428 has a different central axis than elongated member 418. In other embodiments, elongated member 418 may have multiple conduits that each may accept shaft 430 of stylet 425. Stylet 425 may be used within only one of the multiple conduits or moved to different conduits as the clinician needs to bend lead 416 in a particular direction.

Figure 21:
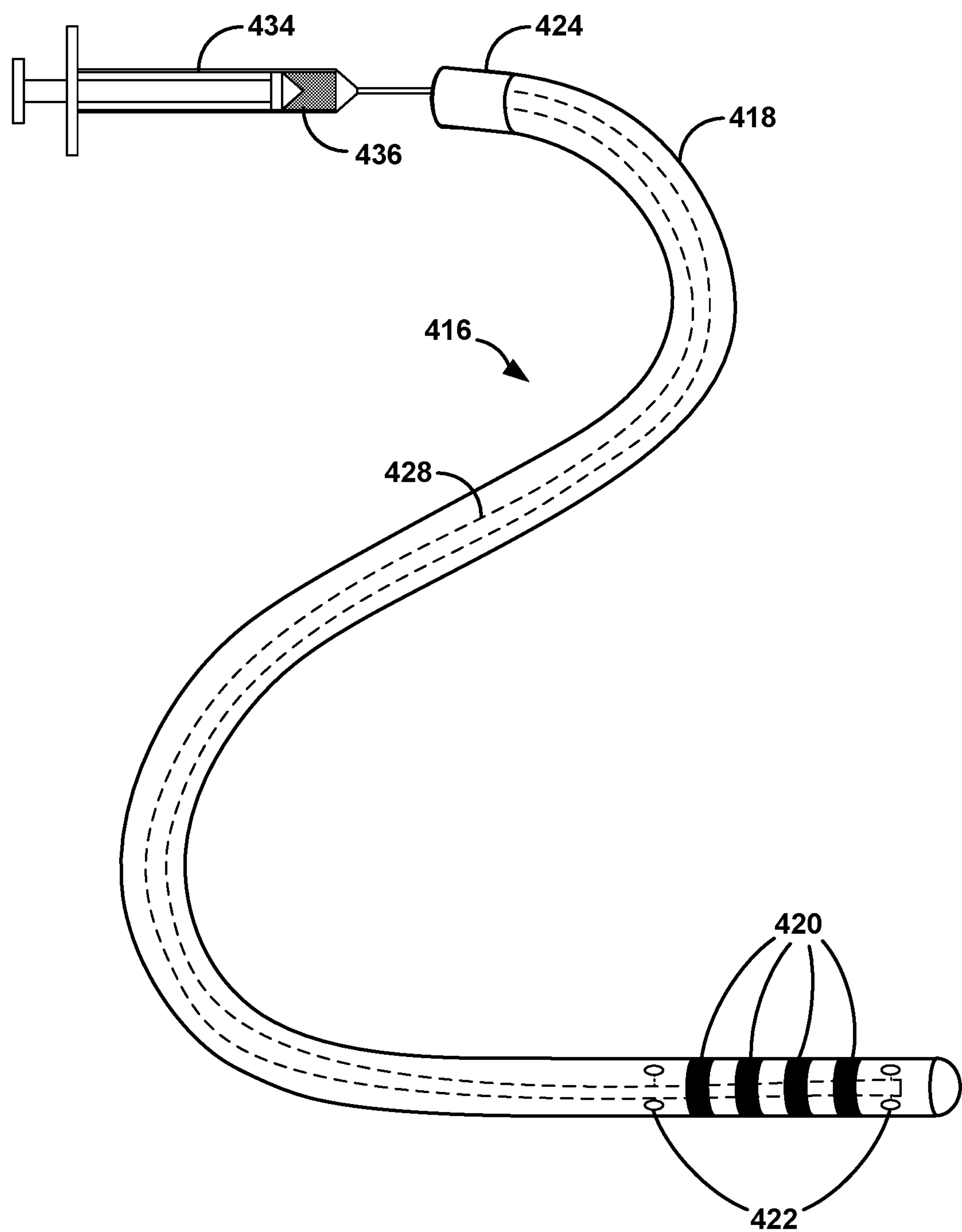
FIG. 21 is a perspective drawing illustrating the injection of a solidifying substance into the lead to form fixation elements.

FIG. 21 is a perspective drawing illustrating the injection of a solidifying substance into the lead to form fixation elements. As shown in FIG. 21, fluid delivery device 434 is used to deliver solidifying substance 436 to conduit 428 of lead 416. Conduit 428 may or may not accept stylet 425, as discussed in FIGS. 20A and 20B. Solidifying substance 436 is forced down conduit 428 and out of exit ports 422 into the adjacent tissue of patient 16. Once solidifying substance 436 creates the fixation elements that secure lead 416 within patient 16, lead 416 may be coupled to an electrical stimulator to deliver electrical stimulation therapy to the target tissue of the patient via electrodes 420. Fixation elements may include any of the fixation elements described herein, including adhesive elements, fixation structures, or balloon elements.

Fluid delivery device 434 is shown as a syringe that the clinician inserts into the end of lead 416 and pushes a plunger of the syringe to inject solidifying substance 436. In some embodiments, fluid delivery device 434 may be a device different than a syringe. For example, fluid delivery device 434 may be a gravity feed bag, an automatic syringe pump, a mechanical fluid pump, or any other fluid delivery device that is configured to deliver solidifying substance 434 into conduit 428. In addition, lead 416 of other embodiments may include another conduit that delivers a therapeutic agent to patient 16 instead of, or in addition to, the electrical stimulation. The therapeutic agent may be one of a pharmaceutical agent, insulin, a pain relieving agent or a gene therapy agent.

Figure 22:
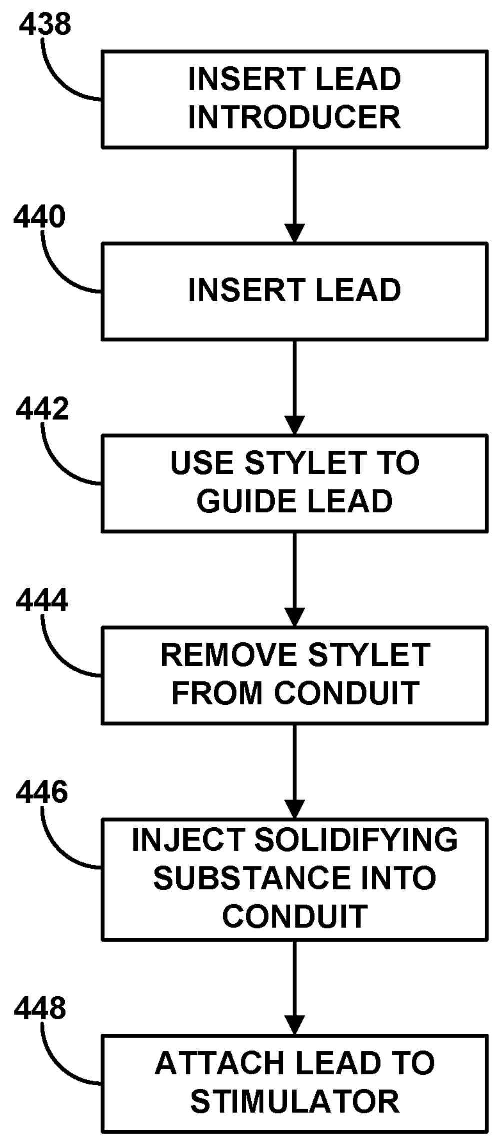
FIG. 22 is a flow diagram illustrating a process for removing a stylet from a conduit in an elongated member and delivering a solidifying substance through the conduit.

FIG. 22 is a flow diagram illustrating a process for removing a stylet from a conduit in an elongated member and delivering a solidifying substance through the conduit during lead implantation. A clinician may implant any of leads 14, 60, 68, 76, 92, 100, 364, 374, 382, 390, or 416 which may use a stylet for inserting the lead into patient 16. However, lead 416 will be referenced as an example. First, the clinician inserts a lead introducer into patient 16 proximate to the target tissue site (438). The tissue site may be near the sacral nerve, occipital nerve, any other nerve which may provide effective therapy to patient 16 or adjacent to any other suitable therapy deliver site. The clinician then inserts lead 416 into the lead introducer (440) and uses stylet 425 to bend and guide lead 416 to the specific location until electrodes 420 of lead 416 are placed correctly in proximity to the target stimulation site (442).

The clinician next removes stylet 425 from conduit 428 of elongated member 418 (444). The clinician then attaches fluid delivery device 434 (FIG. 21), and injects the solidifying substance through conduit 428 and through exit ports 422 to fix lead 416 within patient 16 (446). Once the solidifying substance is cured, the clinician attaches conductor 424 of lead 416 to stimulator 12. (448). In some embodiments, lead 416 may include more than one conduit which delivers the solidifying substance and/or accepts shaft 430 of stylet 425.

Many embodiments of the invention have been described. Various modifications may be made without departing from the scope of the claims. For example, the present invention further includes within its scope methods of making and using systems and leads for stimulation, as described herein, as well as methods of making and using elongated members for therapy systems. Also, the elongated members described herein may have a variety of therapy applications, such as fluid delivery to a target therapy deliver site or other electrical stimulation applications (e.g., sensing or delivery of cardiac electrical stimulation, including paces, pulses, and shocks). These and other embodiments are within the scope of the following claims.

The invention claimed is:

1. A method comprising:

inserting a medical elongated member into a patient, wherein the medical elongated member comprises one or more electrodes and an adhesive element disposed on a longitudinal outer surface of the medical elongated member, the adhesive element being disposed on and pre-bonded to the longitudinal outer surface of the elongated member, wherein the adhesive element is disposed on the outer surface of the elongated member at a location distal to all of the one or more electrodes of the medical elongated member;

positioning the medical elongated member adjacent to or at a target therapy delivery site; and subsequent to inserting the medical elongated member into the patient, exposing the adhesive element to moisture to activate the adhesive element and secure the elongated member adjacent to the target therapy delivery site.

2. The method of claim 1, wherein exposing the adhesive element to moisture comprises removing a sheath that encloses at least a portion of the medical elongated member and covers the adhesive element.

3. The method of claim 2, wherein removing the sheath comprises removing the sheath that covers the one or more electrodes.

4. The method of claim 2, wherein removing the sheath exposes the adhesive element to the moisture within at least one of a bodily fluid or body tissue to activate the adhesive element.

5. The method of claim 1, wherein inserting the medical elongated member into the patient comprises introducing an introducer proximate to a peripheral nerve of the patient.

6. The method of claim 5, wherein introducing the introducer proximate to the peripheral nerve comprises positioning the introducer substantially transversely across an occipital nerve.

7. The method of claim 1, further comprising coupling the medical elongated member to a medical device, the medical device being configured to deliver electrical stimulation therapy to the patient.

8. The method of claim 7, further comprising controlling the medical device to deliver electrical stimulation therapy via the medical device and medical elongated member.

9. The method of claim 1, wherein the adhesive element comprises a plurality of adhesive elements disposed around a circumference of the longitudinal outer surface of the elongated member.

10. The method of claim 1, further comprising:

delivering an energy that deactivates the adhesive element via at least one conduit disposed within the medical elongated member; and explanting the medical elongated member from the patient.

11. The method of claim 1, further comprising introducing a solvent into the patient to deactivate the adhesive element, wherein the solvent is configured to react with the adhesive element to deactivate the adhesive element.

12. The method of claim 1, wherein the target therapy delivery site is at least one of a sacral nerve, a pudendal nerve, a spinal cord, or an occipital nerve.

13. The method of claim 1, wherein the adhesive element comprises a material that comprises one of 2-octyl cyanoacrylate or fibrin glue.

14. A method comprising:

inserting a medical elongated member into a patient, wherein the medical elongated member comprises one or more electrodes and an adhesive element disposed on a longitudinal outer surface of the medical elongated member, the adhesive element being disposed on and pre-bonded to the longitudinal outer surface of the medical elongated member, wherein the adhesive element is disposed on the outer surface of the elongated member at a location distal to all of the one or more electrodes of the medical elongated member;

positioning at least one electrode of the one or more electrodes adjacent to or at a target therapy delivery site; and subsequent to positioning the at least one electrode adjacent to the target therapy delivery site, exposing the adhesive element to moisture to activate the adhesive element and secure, adjacent to the target therapy delivery site, the medical elongated member and the at least one electrode.

15. The method of claim 14, wherein exposing the adhesive element to moisture comprises removing a sheath that encloses at least a portion of the medical elongated member and covers the adhesive element.

16. The method of claim 15, wherein removing the sheath exposes the adhesive element to the moisture within at least one of a bodily fluid or body tissue to activate the adhesive element.

17. The method of claim 14, further comprising coupling the medical elongated member to an electrical stimulator configured to deliver electrical stimulation therapy to the patient via the at least one electrode of the medical elongated member.

18. The method of claim 14, wherein inserting the medical elongated member into the patient comprises introducing an introducer proximate to a peripheral nerve of the patient.

19. The method of claim 14, wherein the adhesive element comprises a material that comprises one of 2-octyl cyanoacrylate or fibrin glue.

* * * * *